(12) United States Patent
Bastian et al.

(10) Patent No.: US 8,501,404 B2
(45) Date of Patent: Aug. 6, 2013

(54) GNAQ MUTATIONS IN MELANOMA

(75) Inventors: Boris C. Bastian, Mill Valley, CA (US); Catherine D. Van Raamsdonk, Vancouver (CA); Gregory S. Barsh, San Mateo, CA (US)

(73) Assignees: The Regents of the University of California, Oakland, CA (US); The Board of Trustees of the Leland Stanford Junior University, Palo Alto, CA (US); The University of British Columbia, Vancouver, BC (CA)

( * ) Notice: Subject to any disclaimer, the term of this patent is extended or adjusted under 35 U.S.C. 154(b) by 453 days.

(21) Appl. No.: 12/526,449

(22) PCT Filed: Feb. 8, 2008

(86) PCT No.: PCT/US2008/053484
§ 371 (c)(1), (2), (4) Date: Dec. 6, 2010

(87) PCT Pub. No.: WO2008/098208
PCT Pub. Date: Aug. 14, 2008

(65) Prior Publication Data
US 2011/0070221 A1  Mar. 24, 2011

Related U.S. Application Data

(60) Provisional application No. 60/900,479, filed on Feb. 8, 2007.

(51) Int. Cl.
*C12Q 1/68* (2006.01)

(52) U.S. Cl.
USPC .......................................................... 435/6.1

(58) Field of Classification Search
None
See application file for complete search history.

(56) References Cited

FOREIGN PATENT DOCUMENTS

| WO | WO 2004/043232 A2 | 5/2004 |
|----|----|----|
| WO | WO 2005/047542 A1 | 5/2005 |
| WO | WO 2005/059171 A1 | 6/2005 |

OTHER PUBLICATIONS

Burgess et al. (J. Cell Biol. 111:2129-2138, 1990).*
Lazar et al. ( Mol. Cell Biol. 8:1247-1252, 1998).*
Tockman et al (Cancer Res., 1992, 52:2711s-2718s).*
Bamford et al (British Journal of Cancer, 2004, 91: 355-358).*
Sausville et al (Journal of Clinical Oncology, 2001, 19(8): 2319-2333).*
Ariyanayagam-Baksh et al.; "Malignant blue nevus: a case report and molecular analysis"; *Am. J. Dermatopathol*; 25(1):21-27 (2003).
Bamford et al.; "The COSMIC (Catalogue of Somatic Mutations in Cancer) database and website"; *Br. J. Cancer*; 91: 355-358 (2004).
COSMIC Mutation id 18200; Gene GNAQ http://www.sanger.ac.uk/perl/genetics/CGP/cosmic?action=mut_summary&id=18200 accessed Aug. 27, 2009 (1 page).
COSMIC id 753546; Sample Name CP66-MEL http://www.sanger.ac.uk/perl/genetics/CGP/cosmic?action=sample;id=753546 Accessed Aug. 27, 2009 (6 pages).
Curtin et al.; "Distinct Sets of Genetic Alterations in Melanoma"; *N. Engl. J. Med* .; 353(20): 2135-2147 (2005).
Fisher et al.; "Meeting report: fourth international congress of the Society for Melanoma Research"; *Pigment Cell &Melanoma Research*. 21(1): 15-26 (2008).
Kalinec et al.; "Mutated α subunit of the $G_p$ protein induces malignant transformation in NIH 3T3 cells"; *Mol. Cell. Biol.*; 12(10): 44687-4693 (1992).
Lopez et al.; "Ocular malignant melanoma and blue nevi"; *Am J Dermatopathol.*; 20(1):109-110 (1998).
Navenot et al.; "Kisspeptin-10-induced signaling of GPR54 negatively regulates chemotactic responses mediated by CXCR4: a potential mechanism for the metastasis suppressor activity of kisspeptins"; *Cancer Res.*; 65(22): 10450-10456 (2005).
Neves et al.; "G protein pathways"; *Science*; 296: 1636-1639 (2002).
Onken et al.; "Oncogenic mutations in GNAQ occur early in visual melanoma"; 2008; *Investigative Opthalmology & Visual Science*; manuscript published on Aug. 21, 2008.
Pollock et al.; "Melanoma mouse model implicates metabotropic glutamate signaling in melanocytic neoplasia"; *Nat. Genet*; 34(1):108-112 (2003).
Singh et al.; "Lifetime prevalence of uveal melanoma in white patients with oculo(dermal) melanocytosis"; *Ophthalmology*; 105(1):195-198 (1998).
Tschentscher et al.; "Identification of chromosomes 3, 6, and 8 aberrations in uveal melanoma by microsatellite analysis in comparison to comparative genomic hybridization"; *Cancer Genet. Cytogenet.*; 122(1):13-17 (2000).
Van Raamsdonk et al.; "Effects of G-protein mutations on skin color"; *Nature Genetics*; 36(9): 961-968 (2004).
Zuidervaart et al.; "Activation of the MAPK pathway is a common event in uveal melanomas although it rarely occurs through mutation of *BRAF* or *RAS*"; *Br. J. Cancer*; 92: 2032-2038 (2005).
International Search Report and Written Opinion from PCT/US2008/053484, dated Sep. 22, 2008 (15 pages).

* cited by examiner

*Primary Examiner* — Sean Aeder
(74) *Attorney, Agent, or Firm* — Kilpatrick Townsend & Stockton LLP

(57) ABSTRACT

The present invention provides methods of detecting mutations in a Gnaq gene in a melanocytic neoplasm for diagnostic and prognostic purposes. The invention further provides methods of treating such melanocytic neoplasm by modulating the activity of the mutated Gnaq gene.

25 Claims, 3 Drawing Sheets

SEQUENCE LISTING

<160> NUMBER OF SEQ ID NOS: 15

<210> SEQ ID NO 1
<211> LENGTH: 2188
<212> TYPE: DNA
<213> ORGANISM: Homo sapiens
<220> FEATURE:
<223> OTHER INFORMATION: guanine nucleotide binding protein (G protein)
      q polypeptide (GNAQ, GAQ, G-alpha-q, Galphaq) cDNA
<220> FEATURE:
<221> NAME/KEY: CDS
<222> LOCATION: (42)..(1121)
<223> OTHER INFORMATION: Gnaq

<400> SEQUENCE: 1

```
agggggtgcc ggcggggctg cagcggaggc actttggaag aatgactctg gagtccatca      60
tggcgtgctg cctgagcgag gaggccaagg aagcccggcg gatcaacgac gagatcgagc     120
ggcagctccg cagggacaag cgggacgccc gccgggagct caagctgctg ctgctcggga     180
caggagagag tggcaagagt acgtttatca gcagatgaa aatcatccat gggtcaggat     240
actctgatga agataaaagg ggcttcacca agctggtgta tcagaacatc ttcacggcca     300
tgcaggccat gatcagagcc atggacacac tcaagatccc atacaagtat gagcacaata     360
aggctcatgc acaattagtt cgagaagttg atgtggagaa ggtgtctgct tttgagaatc     420
catatgtaga tgcaataaag agtttatgga atgatcctgg aatccaggaa tgctatgata     480
gacgacgaga atatcaatta tctgactcta ccaaatacta tcttaatgac ttggaccgcg     540
tagctgaccc tgcctacctg cctacgcaac aagatgtgct tagagttcga gtccccacca     600
cagggatcat cgaataccc tttgacttac aaagtgtcat tttcagaatg gtcgatgtag     660
ggggccaaag gtcagagaga agaaaatgga tacactgctt tgaaaatgtc acctctatca     720
tgtttctagt agcgcttagt gaatatgatc aagttctcgt ggagtcagac aatgagaacc     780
gaatggagga aagcaaggct ctctttagaa caattatcac ataccctgg ttccagaact     840 cctcggttat tctgttctta aacaagaaag atcttctaga ggagaaaatc atgtattccc     900
atctagtcga ctacttccca gaatatgatg gaccccagag agatgcccag gcagcccgag     960
aattcattct gaagatgttc gtggacctga acccagacag tgacaaaatt atctactccc    1020
acttcacgtg cgccacagac accgagaata tccgctttgt ctttgctgcc gtcaaggaca    1080
ccatcctcca gttgaacctg aaggagtaca atctggtcta attgtgcctc ctagacaccc    1140
gccctgccct tccctggtgg gctattgaag atacacaaga gggactgtat ttctgtggaa    1200
aacaatttgc ataatactaa tttattgccg tcctggactc tgtgtgagcg tgtccacaga    1260
```

```
gtttgtagta aatattatga ttttatttaa actattcaga ggaaaaacag aggatgctga    1320
agtacagtcc cagcacattt cctctctatc ttttttttag gcaaaacctt gtgactcagt    1380
gtattttaaa ttctcagtca tgcactcaca aagataagac ttgtttcttt ctgtctctct    1440
ctcttttctt tttctatgga gcaaaacaaa gctgatttcc cttttttctt cccccgctaa    1500 ttcataccte cctcctgatg ttttttcccag gttacaatgg cctttatcct agttccattc    1560
ttggtcaagt ttttctctca aatgatacag tcaggacaca tcgttcgatt taagccatca    1620
tcagcttaat ttaagtttgt agttttttgct gaaggattat atgtattaat acttacggtt    1680
ttaaatgtgt tgctttggat acacacatag tttcttttt aatagaatat actgtcttgt    1740
ctcactttgg actgggacag tggatgccca tctaaaagtt aagtgtcatt tcttttagat    1800
gtttaccttc agccatagct tgattgctca gagaaatatg cagaaggcag gatcaaagac    1860
acacaggagt ccttttcttt gaaatgccac gtgccattgt cttcctccc ttctttgctt    1920 cttttttctta ccctctcttt caattgcaga tgccaaaaaa gatgccaaca gacactacat    1980
taccctaatg gctgctaccc agaaccttt tataggttgt tcttaattt tttgttgttg    2040 ttgttcaagc ttttccttc tttttttct tagtgtttgg gccacgattt taaaatgact    2100
tttattatgg gtatgtgttg ccaaagctgg ctttttgtca aataaaatga atacgaactt    2160
aaaaaataaa aaaaaaaaa aaaaaaaa                                        2188
```

<210> SEQ ID NO 2
<211> LENGTH: 359
<212> TYPE: PRT
<213> ORGANISM: Homo sapiens
<220> FEATURE:
<223> OTHER INFORMATION: guanine nucleotide binding protein (G protein)
      q polypeptide (Gnaq, GAQ, G-alpha-q, Galphaq)

<400> SEQUENCE: 2

```
Met Thr Leu Glu Ser Ile Met Ala Cys Cys Leu Ser Glu Glu Ala Lys
  1               5                  10                  15

Glu Ala Arg Arg Ile Asn Asp Glu Ile Glu Arg Gln Leu Arg Arg Asp
             20                  25                  30

Lys Arg Asp Ala Arg Arg Glu Leu Lys Leu Leu Leu Leu Gly Thr Gly
         35                  40                  45

Glu Ser Gly Lys Ser Thr Phe Ile Lys Gln Met Arg Ile Ile His Gly
     50                  55                  60

Ser Gly Tyr Ser Asp Glu Asp Lys Arg Gly Phe Thr Lys Leu Val Tyr
 65                  70                  75                  80

Gln Asn Ile Phe Thr Ala Met Gln Ala Met Ile Arg Ala Met Asp Thr
                 85                  90                  95

Leu Lys Ile Pro Tyr Lys Tyr Glu His Asn Lys Ala His Ala Gln Leu
            100                 105                 110

Val Arg Glu Val Asp Val Glu Lys Val Ser Ala Phe Glu Asn Pro Tyr
        115                 120                 125

Val Asp Ala Ile Lys Ser Leu Trp Asn Asp Pro Gly Ile Gln Glu Cys
    130                 135                 140

Tyr Asp Arg Arg Arg Glu Tyr Gln Leu Ser Asp Ser Thr Lys Tyr Tyr
145                 150                 155                 160

Leu Asn Asp Leu Asp Arg Val Ala Asp Pro Ala Tyr Leu Pro Thr Gln
                165                 170                 175

Gln Asp Val Leu Arg Val Arg Val Pro Thr Thr Gly Ile Ile Glu Tyr
            180                 185                 190

Pro Phe Asp Leu Gln Ser Val Ile Phe Arg Met Val Asp Val Gly Gly
```

```
            195                 200                 205
Gln Arg Ser Glu Arg Arg Lys Trp Ile His Cys Phe Glu Asn Val Thr
210                 215                 220

Ser Ile Met Phe Leu Val Ala Leu Ser Glu Tyr Asp Gln Val Leu Val
225                 230                 235                 240

Glu Ser Asp Asn Glu Asn Arg Met Glu Glu Ser Lys Ala Leu Phe Arg
                245                 250                 255

Thr Ile Ile Thr Tyr Pro Trp Phe Gln Asn Ser Ser Val Ile Leu Phe
                260                 265                 270

Leu Asn Lys Lys Asp Leu Leu Glu Glu Lys Ile Met Tyr Ser His Leu
            275                 280                 285

Val Asp Tyr Phe Pro Glu Tyr Asp Gly Pro Gln Arg Asp Ala Gln Ala
        290                 295                 300

Ala Arg Glu Phe Ile Leu Lys Met Phe Val Asp Leu Asn Pro Asp Ser
305                 310                 315                 320

Asp Lys Ile Ile Tyr Ser His Phe Thr Cys Ala Thr Asp Thr Glu Asn
                325                 330                 335

Ile Arg Phe Val Phe Ala Ala Val Lys Asp Thr Ile Leu Gln Leu Asn
                340                 345                 350

Leu Lys Glu Tyr Asn Leu Val
        355

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:antisense
      RNA for depleting protein kinase C (PKC) alpha mRNA

<400> SEQUENCE: 3
gttctcgctg gtgagtttca                                               20

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:synthetic
      GNAQ exon 5 PCR primer

<400> SEQUENCE: 4
cccacaccct actttctatc atttac                                        26

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:synthetic
      GNAQ exon 5 PCR primer, Gnaq Q209 mutation PCR primer

<400> SEQUENCE: 5 ttttcccctaa gtttgtaagt agtgc                                        25

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:synthetic
      peptide nucleic acid (PNA) for detecting Gnaq Q209 mutations
<220> FEATURE:
```

```
<221> NAME/KEY: modified_base
<222> LOCATION: (1)..(15)
<223> OTHER INFORMATION: peptide nucleic acid (PNA), phosphodiester
      backbone replaced by peptide backbone
<220> FEATURE:
<221> NAME/KEY: modified_base
<222> LOCATION: (1)
<223> OTHER INFORMATION: t modified by acetyl (Ac) group
<220> FEATURE:
<221> NAME/KEY: modified_base
<222> LOCATION: (15)
<223> OTHER INFORMATION: c modified by amide group (-CONH-2)

<400> SEQUENCE: 6
tctctgacct ttggc                                                           15

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:synthetic
      Gnaq Q209 mutation PCR primer

<400> SEQUENCE: 7
atccattttc ttctctctga cc                                                   22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence:synthetic
      pool 1 siRNA

<400> SEQUENCE: 8
caauaaggcu caugcacaau u                                                    21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence:synthetic
      pool 1 siRNA

<400> SEQUENCE: 9
cgacgagaau aucaauuauu u                                                    21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence:synthetic
      pool 1 siRNA

<400> SEQUENCE: 10
gcaagaguac guuuaucaau u                                                    21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence:synthetic
      pool 1 siRNA

<400> SEQUENCE: 11
```

-continued uaguagcgcu uagugaauau u                                    21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence:synthetic
      pool 2 siRNA

<400> SEQUENCE: 12
augcacaauu aguucgagau u                                    21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence:synthetic
      pool 2 siRNA

<400> SEQUENCE: 13
uaugauagac gacgagaauu u                                    21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence:synthetic
      pool 2 siRNA

<400> SEQUENCE: 14
cagacaauga gaaccgaauu u                                    21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence:synthetic
      pool 2 siRNA

<400> SEQUENCE: 15
cgccacagac accgagaauu u                                    21

GNAQ MUTATIONS IN MELANOMA

CROSS-REFERENCE TO RELATED APPLICATIONS

This application is the U.S. National Stage entry under §371 of International Application No. PCT/US2008/053484, filed Feb. 8, 2008, which claims benefit of U.S. provisional application No. 60/900,479; filed: Feb. 8, 2007; the disclosures of each are herein incorporated by reference in their entirety for all purposes.

STATEMENT AS TO RIGHTS TO INVENTIONS MADE UNDER FEDERALLY SPONSORED RESEARCH OR DEVELOPMENT

This invention was made with Government support under grant no. P01 CA 025874-25-A1 awarded by the National Institutes of Health. The Government has certain rights in this invention.

BACKGROUND OF THE INVENTION

The current model of melanoma formation is that melanocytes progress from a normal to malignant state by accumulating mutations in key melanoma genes. See, Meier, F., et al. (1998) *Frontiers in Bioscience* 3:D1005-1010. Melanoma can arise spontaneously, or within a pre-existing nevus or mole. Nevi possess mutations in known melanoma genes and are therefore a risk factor for developing melanoma. See, e.g., Pollock, P. M., et al., (2003) Nat. Genet. 33(1):19-20; Kumar, R. et al., (2004) *J. Invest. Dermatol.* 122(2):342-348; Chinm L., (2003) *Nat. Rev. Cancer* 3(8):559-570.

The majority of human melanomas and melanocytic nevi have been shown to have activating mutations in the BRAF, NRAS, C-KIT, or HRAS genes. Furthermore, recent studies have demonstrated that mealnomas fall into genetically distinct groups having marked differences in the frequency of MAP-kinase pathway activation. See, Curtin, J. A., et al., (2005) *N Engl J Med.* 353(20):2135-47. One category, uveal melanoma, arises from melanocytes within the choroidal plexus of the eye and is biologically distinct from cutaneous melanoma by characteristic cytogenetic alterations. See, Horsman et al. (1993) *Cancer* 71(3):811. The other category are intradermal melanocytic proliferations, which can be congenital or acquired, and present in diverse ways ranging from discrete bluish moles (blue nevi) to large blue-gray patches affecting the conjunctiva and periorbital skin (nevus of Ota), shoulders (nevus of Ito), and the lower back (Mongolian spot). See, Zembowicz, et al. (2004) *Histopathology* 45(5): 433. These intradermal melanocytic proliferations do not contain either BRAF or NRAS mutations, and thus have a unique eitiology when compared with other nevi and melanoma. See, Ariyanayagam-Baksh S M, et al., (2003) *Am J Dermatopathol.* 25(1): p. 21-7. Uveal melanomas display MAP-kinase activation (See, Zuidervaat et al. (2005) *British J. Cancer* 92(11):2032) but typically do not have mutations in BRAF, NRAS, or KIT. Although uveal melanoma is diagnosed in the United States at a rate of 4.3-6 cases per million per year, a previous study of 1250 Caucasians with uveal melanoma found only 17 patients (1.4%) with ocular or oculodermal melanocytosis. See, Gonder J. R., et al., (1982) *Ophthalmology,* 89(8): 953-60. A potential connection between intradermal melanocytic neoplasms and uveal melanomas is suggested by the fact that nevus of Ota is a risk factor for uveal melanoma and by an overlap in some of the histo-morphological features of the two conditions, and the two have been reported to occur together. See, Lopez, M. T., et al., (1998) *Am J Dermatopathol.* 20:109-110; Singh, A. D., et al. (1998) *Opthamol.* 105(1):195.

Recently, a large-scale mutagenesis screen in mice identified several dark skin (Dsk) mutants. See, Van Raamsdonk C D, et al., (2004) *Nat Genet.* 36: 961-968. Some of these mutants had a melanocytic phenotype with a sparse cellular proliferation of intradermal melanocytes resembling blue nevi. The mutations were shown to be the result of mutations in G-protein α-subunits.

G proteins represent a large family of heterotrimeric proteins found in mammals composed of alpha (α), beta (β) and gamma (γ) subunits. See, Wettschureck, N. A. O. S., (2005) *Physiol. Rev.* 85(4):1159-1204. G-αq, is one of a variety of G-alpha subunits that mediates the stimulation of phospholipase Cβ through the binding and hydrolysis of GTP. See, Markby, D. W., et al., (1993) *Science* 262(1541):1895-1901. It has been hypothesized that activation of G-αq promotes the survival of melanocytes in the dermis. See, Van Raamsdonk, C. D., et al., (2004). This is consistent with the observation in mice that hyperactivity of G-αq increases the number of melanoblasts, immature melanocytes, migrating in the dermis without increasing their mitotic rate. See, Van Raamsdonk, C. D., et al., (2004).

Germline hypermorphic mutations in Gαq in mice cause dermal hyperpigmentation, without altering epidermal pigmentation. For example, the Gnaq$^{Dsk1}$ and Gnaq$^{Dsk10}$ mutations are considered to be hyperactive, rather than constitutive because they do not occur in amino acids essential for GTPase activity and remain dependent upon a functioning G protein coupled to the Endothelin B receptor. See, Van Raamsdonk, C. D., et al., (2004). Notably, the Gnaq$^{Dsk1}$ and Gnaq$^{Dsk10}$ mice do not develop tumors. See, Van Raamsdonk, C. D., et al (2004). However, blocking the GTPase activity through the substitution of critical amino acids can result in constitutive activation. See, Markby, D. W., et al. (1993). For example, a mutation of Q227 in Gαs (Gnas) causes constitutive activity in human pituitary tumors. See, Landis, C. A., et al. (1989) *Nature* 340(6236):692-696.

Transgenic mice ectopically expressing the G-protein coupled receptor Grm-1 in melanocytes have both dermal hyperpigmentation and large melanocytic tumors. See, Pollock, P. M., et al. (2003) *Nat. Genet.* 34(1):108-112. Furthermore, injections of constituitively active-Gnaq transformed NIH3T3 cells into athymic nude mice induce tumors within 1 week of injection. See, Kaqlinec G. et al. (1992) *Mol. Cell Biol.* 12(10):4687-4693.

One mutation in Gnaq has been reported as being present in a melanoma sample. This mutation is described in the Sanger Institute Catalogue Of Somatic Mutations In Cancer (COSMIC) web site on the world wide web at sanger.ac/uk/cosmic. See, Bamford et al (2004) *Br J Cancer,* 91:355-358. The mutation (Mutation ID No. 18200) described in COSMIC sample id no: 753546 (sample name CP66-MEL) is a missense substitution mutation (1075 G to A) resulting in a conservative amino acid substitution (V359I). There is no teaching that the V359I conservative missense mutation of Gnaq in CP66-MEL, has any effect on Gnaq activity.

The current invention is based, in part, on the discovery that activated Gα subunits resulting from mutations in Gnaq, e.g., mutations that constitutively activate Gnaq, are present in melanocytic neoplasms, e.g., blue nevi, such as nevi of Ota; malignant blue nevi, a rare type of melanoma arising from a blue nevus (see, Granter, S. R., et al., (2001) *Am. J. Surg. Pathol.* 25(3):316-323); uveal and certain cutaneous melanomas, e.g., lentigo maligna melanoma or melanomas from skin that is damaged by chronic sun exposure (CSD melanoma).

BRIEF SUMMARY OF THE INVENTION

The current invention provides methods of detecting a melanoma or nevus cell in a biological sample. The methods comprise detecting an activating sequence mutation in a Gnaq gene in a biological sample comprising the suspected melanoma cell or nevus cell from a patient. For example, the invention provides methods of detecting melanoma, e.g., uveal, malignant blue nevi, or CSD melanoma (including lentigo maligna melanoma), by detecting the presence of a mutation in a Gnaq gene or product encoded by the gene; or by detecting overexpression of Gnaq. The methods can be used for diagnostic and prognostic indications and, for identifying melanoma patients that are responsive, or likely to be responseive, to various treatment therapies, e.g., G-alpha antagonists, or therapies that target downstream signaling components, such as protein kinase C inhibitors. The invention also provides methods of treating melanoma comprising administering a Gnaq inhibitor to a patient having a melanoma, e.g., a uveal melanoma, malignant blue nevus, or CSD melanoma, arising from a mutation in a Gnaq gene.

Thus, the invention provides a method of detecting a melanocytic neoplasm in a biological sample, e.g., a skin or eye sample, comprising melanoma cells from a patient, e.g., a patient that has, or is suspected of having, melanoma, the method comprising detecting a sequence mutation of Gnaq in melanoma or nevi cells present in the biological sample, wherein the presence of an activating mutation of Gnaq is indicative of the presence of a melanocytic neoplasm. In some embodiments, the melanocytic neoplasm is a uveal melanoma, a melanoma that arises on skin having damage induced from chronic sun exposure, e.g., a lentigo maligna melanoma, or a melanoma arising in a nevus, e.g., malignant blue nevus. In other embodiments, the melanocytic neoplasm may be an acral lentiginous melanoma, mucosal melanoma, nodular melanoma, superficial spreading melanoma, desmoplastic melanoma, or a melanoma arising in a congenital nevus, or metastases. In other embodiments, the Gnaq mutation is indicative of a nevus, such as a blue nevus, nevus of Ota, an atypical blue nevus, an atypical cellular blue nevus, a blue nevus with neurocristic hamartoma, or a blue nevus without specific diagnosis. In other embodiments, the nevus can be a congenital nevus, or a deep penetrating nevus. In some embodiments, the detecting step comprises detecting the presence or absence of a Gnaq mutation in a nucleic acid, e.g., mRNA or genomic DNA. In typical embodiments, such detection steps comprise an amplification reaction, such as PCR or RT-PCR, in situ hybridization, or electrophoretic nucleic acid separation (e.g., northern or Southern blotting). In other embodiments, the detecting step comprises detecting the mutation in a Gnaq protein, e.g., measuring the level of Gnaq activity and/or expression. In typical embodiments, such detecting step comprises the use of antibodies (immunocytochemistry) and/or electrophorectic protein separation (e.g., western blot). In some embodiments the Gnaq mutation is Gln209 to Leu (CAA to CTA or CAA to TTA), while in other embodiments, the Gnaq mutation is Gln209 to Pro (C AA to CCA). In some embodiments the Gnaq mutation is Gln 209 to Arg (CAA to CGA). In still other embodiments the Gnaq mutation is Gln 209 to Tyr (CAA to TAT).

Typically, the detecting step comprises detecting the presence or absence of a sequence mutation in a Gnaq. This is often achieved, e.g., by analyzing a nucleic acid sample from the biological sample. The nucleic acid can be a DNA or RNA sample. The DNA sample can be obtained from reverse transcription of RNA, or can be genomic DNA. Often, the detection step for detecting the mutation comprises an amplification reaction. The presence or absence of the mutations can be identified, e.g., by sequence analysis of the amplified nucleic acid; or by methods that employ allele-specific oligonucleotide primers or probes.

In some embodiments, the biological sample is from a patient that has, or is suspected of having a melanoma, e.g., uveal melanoma, a melanoma on sun damaged skin, or a malignant blue nevus or metastasis. In other embodiments, the biological sample is from a patient that has, or is suspected of having, a nevus, e.g., a conventional blue nevus, a nevus of Ota, a nevus of Ito, a mongolian spot, an atypical blue nevus, an atypical cellular blue nevus, a blue nevus with neurocristic hamartoma, a blue nevus without specific diagnosis, a congenital nevus, or a deep penetrating nevus.

The invention also provides a method of monitoring progression of melanoma in a patient subjected to a therapy for treatment of the melanoma arising from a mutation in Gnaq. The method comprises detecting a change in the number of cells having a mutation in Gnaq in a biological sample from a patient, where the change in the number of cells having a mutation is indicative of the patient's response to the therapy.

In some embodiments, monitoring progression of melanoma in a patient where the melanoma arose from a mutation in a Gnaq gene is performed by detecting the mutation in a nucleic acid from the biological sample. In other embodiments, the progression of the melanoma arising from a mutation in Gnaq is detected in by evaluating a Gnaq protein present in the biological sample. In some embodiments, the biological sample is from eye or skin. In other embodiments, the biological sample is from blood, lymph node, liver, adrenal gland, or bone.

Typically, in monitoring melanoma progression in accordance with the invention, the presence of a reduced number of cells having a Gnaq mutation in the biological sample taken from a patient after treatment with an agent as compared to the number of cells having a Gnaq mutation in a biological sample taken from the patient before being exposure to the treatment agent is indicative of a positive therapeutic response to the treatment agent.

In all of the detection methods of the invention the biological sample can be from any source in the body that is suspected of containing primary or metastatic melanoma cells. Thus, the biological sample can be from skin, e.g., acral skin; skin having damage from chronic sun exposure, eye, e.g., uvea, conjunctiva, or mucosal membranes. In other embodiments, the sample can be from blood, serum, tissue from lymph nodes, or tissue from visceral organs. In some embodiments, for example in monitoring progression of melanoma, the sample is from a readily accessible tissue such as blood.

In another aspect, the invention provides a method of determining whether a melanoma patient is a candidate for receiving a therapy that inhibits the activity of a Gα subunit, either directly or by inhibiting a protein that is activated by Gα. The method comprises determining whether the melanoma cells have an activating mutation in Gnaq. This determination is performed in accordance with the detection methods described herein. Accordingly, the detecting step can comprise detecting the mutation in mRNA, DNA, or protein. In some embodiments, the detecting step can comprise detecting the presence of a Gnaq mutation in a nucleic acid sample from the melanoma or nevus, whereas in other embodiments, the detecting step is from a protein sample from a melanocytic neoplasm. The nucleic acid sample can be RNA or DNA, e.g., genomic DNA or cDNA made from RNA from the melanocytic neoplasm sample. Often, the detecting step comprises an amplification reaction, such as PCR or RT-PCR.

In some embodiments, the melanoma is a uveal melanoma, a malignant blue nevus, a CSD melanoma, e.g., a lentigo maligna, an acral melanoma, a mucosal melanoma, melanoma, or a superficial spreading melanoma.

In another aspect, the invention provides a method of inhibiting growth and/or proliferation of nevus or melanoma cells arising from a somatic mutation in Gnaq, the method comprising administering a Gnaq antagonist. The Gnaq antagonist can be e.g., a small molecule, such as edelfosine, a protine kinase C inhibitor, or the staurosporine analogue CPG41251; an antibody; a peptide; or a nucleic acid. Typically, the nevi or melanoma cells are from e.g., uveal melanoma, CSD melanoma, e.g., lentigo maligna melanoma, an acral lentiginous melanoma, mucosal melanoma, nodular melanoma, superficial spreading melanoma, desmoplastic melanoma, metastatic melanoma, or a melanoma arising in a nevus, e.g., arising from a blue nevus (a malignant blue nevus) such as a nevus of Ota, a nevus of Ito, a mongolian spot, an atypical blue nevus, an atypical cellular blue nevus, a blue nevus with neurocristic hamartoma, a blue nevus without specific diagnosis, recurrent cellular blue nevus. The melanoma cells may also arise from a congenital nevus or a deep penetrating nevus.

The invention also provides a method of determining the risk of progression of a nevus to a melanoma, the method comprising detecting the presence or absence of a sequence mutation in a Gnaq gene in a biological sample from the nevus, wherein the presence of the mutation is indicative of increased risk of progression of the nevus to melanoma. In some embodiments, the sequence mutation is a codon encoding Gln 209 of Gnaq. In some embodiments, the nevus is a blue nevus, such as a nevus of Ota, an atypical blue nevus, an atypical cellular blue nevus, a blue nevus neurocristic hamartoma, or a blue nevus without specific diagnosis. In some embodiments, the mutation is detected by evaluating the protein that is encoded by the gene.

DETAILED DESCRIPTION OF THE INVENTION

Introduction

Figures 1A, 1B, 1C:
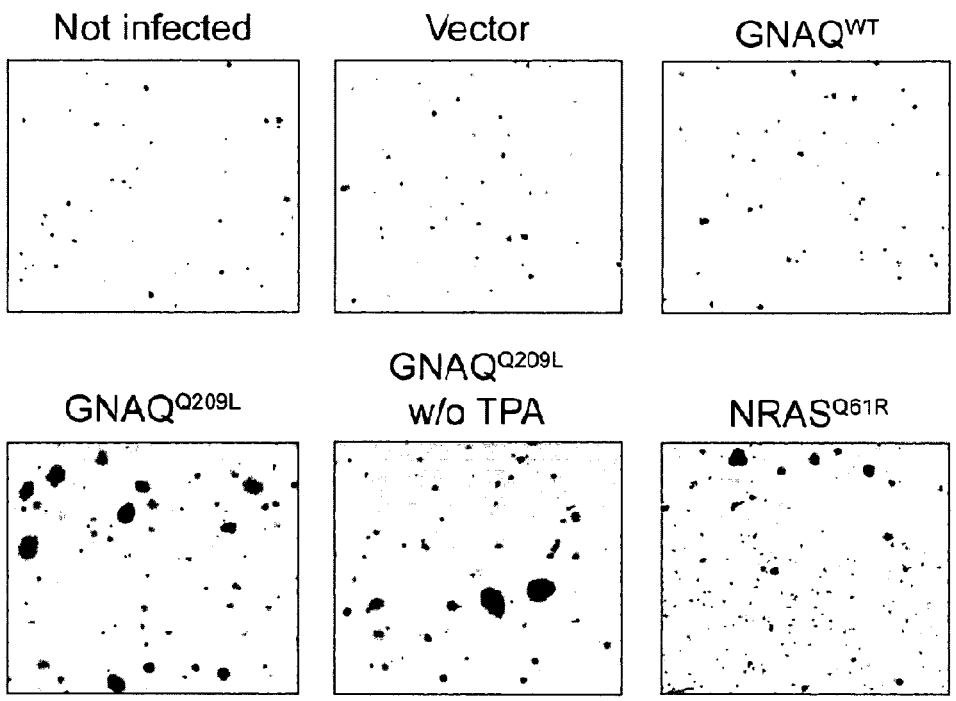
FIG. 1a-1c provides exemplary data showing the effects of expression of mutant and wild-type GNAQ on melanocytes immortalized with hTERT/CDK4$^{R24C}$/p53$^{DD}$. a, GNAQ$^{Q209L}$ induces anchorage independent growth hTERT/CDK4$^{R24C}$/p53$^{DD}$ melanocytes in a TPA-independent manner with comparable efficiency as NRAS$^{Q61R}$. b, Quantitative analysis of colony number and size (mm) of the experiment shown in a. c, Percentage of the cells with morphologically abnormal nuclei.

The present invention provides methods, reagents and kits, for detecting cancer cells for prognostic uses, and for treating melanomas and nevi. The invention is based, in part, upon the discovery that many melanoma and nevi result from activating somatic mutations in Gnaq, i.e., mutations that result in a loss or decrease of GTP hydrolyzing activity of the mutant G-α subunit. Exemplary melanocytic neoplasms that have a Gnaq mutation include uveal melanoma, CSD melanoma (including lentigo maligna melanoma), malignant blue nevus, conventional blue nevus, nevus of Ota, atypical blue nevus, atypical cellular blue nevus, blue nevus neurocristic hamartoma and blue nevus without specific diagnosis.

G-α is the alpha subunit of one of the heterotrimeric GTP-binding proteins that form two subgroups in vertebrates, the widely expressed Gα-q family comprising Gnaq and Gna11, and the Gna14 and Gna15 family, which show more restricted expression. The Gα-q family mediates stimulation of phospholipase Cβ resulting in the hydrolysis of bisphosphoinositide ($PIP_2$) into inositide triphosphate ($IP_3$) and diacylglycerol (DAG). $IP_3$ can stimulate the release of calcium from intracellular storage in the endoplasmic reticulum (ER) leading to downstream calcium-dependent signaling. In parallel, DAG can activate protein kinase C (PKC) and both pathways can then feed into the mitogen activated protein kinase (MAPK) cascade. See, Corbit, K. C., et al., (2000) *Mol. Cell Biol.* 20:5392-5403; Sato, M. et al., (2006) *Ann. Rev. Pharm. Toxicol.* 46:151-187.

The present inventors have discovered that activating mutations in Gnaq, e.g., heterozygous, somatic substitution mutations of Q209 of Gnaq, are present in several types of melanocytic neoplasms, including nevi such as conventional blue nevi, nevi of Ota, atypical blue nevi, atypical cellular blue nevi, blue nevi with neurocristic hamartoma, and blue nevi without specific diagnosis. Interestingly, no other melanoma gene has been previously reported to be mutated in blue nevi, which suggests that blue nevi have a unique etiology compared with other nevi. See, Ariyanayagam-Baksh, S. M., et al., (2003) *Am. J. Dermatopathol.* 25(1):21-27. Activating mutations, e.g., the heterozygous, somatic substitution mutations of Q209 in Gnaq, are also present in a variety of melanomas, including uveal melanoma, malignant blue nevus, CSD melanomas, and lentigo maligna melanoma, a cutaneous melanoma that accounts for about 4-15% of cutaneous melanomas and tends to form in older individuals on sun-exposed sites (see, Chin L., (2003) *Nat. Rev. Cancer.* 3(8): 559-570).

In some embodiments, a Gnaq activating mutation is a mutation that leads to overexpression of Gnaq nucleic acid and polypeptide sequences. Thus, methods that detect levels of Gnaq nucleic acid and/or polypeptide sequences can also be used to detect nevi, e.g., blue nevi, such as nevi of Ota, and melanoma cells as described herein in which Gnaq is overexpressed.

In one aspect of the invention, the ability to detect nevi and/or melanoma cells by virtue of detecting a somatic mutation in Gnaq that activates Gnaq, is useful for any of a large number of applications. For example, it can be used, alone or in combination with other diagnostic methods, to diagnose melanoma, or a certain type of melanoma, in the patient. It can also be used to identify particular melanomas that are sensitive to therapeutics, such as therapeutics that target G-proteins or phospholipase Cβ or other downstream components of pathways regulated by Gnaq.

The detection of somatic activating mutations in Gnaq can also be used to monitor the efficacy of a melanoma treatment. For example, the level of Gnaq activity, e.g., Gα activity, or an activity such as phospholipase Cβ that is dependent on Gα activity, or the numbers of melanocytic cells that have a sequence mutation in Gnaq, after an anti-cancer treatment can be compared to the level before the treatment. A decrease in the level of Gnaq activity, e.g., phospholiapse Cβ activity, or a reduction in the number of melanoma cells that have mutated Gnaq after the treatment indicates efficacious treatment.

The level of Gnaq activity and/or a change in the number of cells having a somatic mutation in Gnaq can also be statistically correlated with the efficacy of particular anti-melanoma therapy or with an observed prognostic outcome, thereby allowing the development of a database on which statistically-based prognosis, or a selection of the most efficacious treatment, can be made in view of a particular level activity or diagnostic presence of a Gnaq mutation.

Detection of cells having an activating mutation in Gnaq can be useful to monitor the number or location of melanoma cells in a patient, for example, to monitor the progression of the cancer over time.

The presence of an activating mutation in Gnaq can also indicate melanomas that are likely to be responsive to therapeutic agents that target mutant Gnaq. Accordingly, the invention also provides methods of treating a melanocytic neoplasm, e.g., uveal melanoma, lentigo maligna melanoma, malignant blue nevus, or melanoma on skin with chronic sun damage, that has an activating mutation in Gnaq by administering a Gα antagonist, e.g., antibodies, peptides, small molecule inhibitors, such as L-threo-dihydrosphingosine (a PKC specific inhibitor) or other small molecule inhibitors, and nucleic acid inhibitors of Gnaq, phospholipase Cβ, or downstream pathways regulated by Gnaq. Such melanocytic neoplasms can be identified by analyzing for the presence of an activating mutation using the methods described herein.

The presence of an activating mutation in Gnaq in nevi often indicates nevi, e.g., conventional types of blue nevi and envi of Ota, that are at risk for progression to melanoma. Accordingly, a nevus from a patient can be evaluated for the presence of an activating mutation using the methods described herein.

DEFINITIONS

The term "Gnaq" refers to the the alpha subunit of a guanine nucleotide binding protein (G-protein). The term encompasses nucleic acid and polypeptide polymorphic variants, alleles, mutants, and fragments of Gnaq. Such sequences are well known in the art. Exemplary human Gnaq sequences are available under the reference sequences NM_002072 in the NCBI nucleotide database (nucleotide sequence) and accession number NP_002063.2 (polypeptide sequence). The sequence NM_002072 is provided as SEQ ID NO:1 as an exemplary nucleotide sequence. The exemplary polypeptide sequence is shown in SEQ ID NO:2.

A "Gnaq-dependent melanoma" as used in the context of this application refers to a melanocytic neoplasm comprising melanoma cells that have a defect (also referred to as a "mutation") in Gnaq that activates Gnaq, i.e., has an "activating" mutation, in comparison to melanocytes that do not have the mutation, and leads to a loss or decrease of GTP hydrolyzing activity of the mutant G-α subunit. The defect in Gnaq can involve a mutation, e.g., a substitution mutation, that results in constitutive activity of the protein. The "Gnaq-dependent melanoma cells" may have one or more of such mutations, e.g, the cells may have somatic substitution mutation involving Q209. A "Gnaq-dependent melanoma" of the present invention can arise, e.g., from sun exposed skin sites, a nevus (e.g., a blue nevus) or the eye (e.g., the uvea). A "Gnaq-dependent melanoma" may also have mutations in genes other than Gnaq.

In the context of this application "acral melanoma" refers to melanoma occurring on the non-hair-bearing skin of the palms or soles or under the nails. A subset of acral melanomas are "acral-lentiginous melanomas"

The term "mucosal melanoma" refers to tumors arising on mucosal membranes; "ocular melanoma" as used herein is melanoma that arises from the eye. "Ocular melanoma" includes uveal and conjunctival melanoma. "Conjunctival melanoma" refers to a melanoma that arises on the conjunctiva, while "uveal melanoma" refers to a melanoma of the pigmented tract of the eye.

"CSD melanoma" as used herein refers to melanoma arising from skin with chronic sun-induced damage; and "NCSD melanoma" as used herein refers to melanoma arising from skin without chronic sun-induced damage. The distinction between the "CSD" and "NCSD" groups in the instant application is based on a microscopic determination of the presence or absence of marked solar elastosis of the dermis surrounding the melanomas. In all but a few cases, melanomas associated with chronic sun-induced damage (CSD) occur on the face and distal extremities such as the forearms, dorsal hands, shins and calfs. These melanomas typically occur in individuals older than 50 years of age, and microscopically, have an intraepidermal component in which melanocytes are arranged as solitary units rather than nests. In addition, these melanomas tend to have an atrophic epidermis with the effacement of the rete ridges. A subset of the CSD melanomas is lentigo maligna melanomas. By contrast melanomas that were not associated with chronic sun-induced damage (NCSD) occur on the trunk and proximal extremities such as thighs and upper arms. The NCSD melanomas typically show an intraepidermal component in which melanocytes are arranged as nests rather than solitary units and display considerable upward scatter (pagetoid spread). Many of the NCSD melanomas are superficial spreading melanomas.

Chronic sun-induced damage is defined as having a CSD score greater than CSD 2. The scores are obtained by determining the degree of solar elastosis on hematoxylin-and-eosin (H&E) stained sections of normal skin surrounding the melanomas at 100-200× magnification using the following system (Landi et al., *Science* 2006), examples of which are provided in FIG. 1:

CSD 0: absence of elastotic fibers; CSD 0+: rare elastotic fibers discernible only at 200× magnification;

CSD 1: scattered elastotic fibers lying as individual units, not as bushels, between collagen bundles; "−" or "+" classifiers were used to indicate whether the elastotic fibers were scarcely or densely scattered.

CSD 2: densely scattered elastotic fibers distributed predominantly as bushels rather than individual units; The "−"classifier was used to indicate that bushels were present, but elastotic fibers distributed as individual units predominated; The "+" classifier was used when larger aggregates of bushels formed, but preserving the outline of individual bushels instead of forming amorphous deposits;

CSD 3: amorphous deposits of blue-gray material with lost fiber texture; "−" only focal formation of amorphous deposits; "+" very large agglomerates of diffuse basophilic material.

As used herein, the term "determining that the melanoma arose from" a site, e.g., acral skin, mucosa, uvea, conjunctiva, or skin having chronic sun-induced damage, refers to identifying the site of origin of a melanoma. Such a determination can be performed by visual inspection of a patient or by a pathology evaluation of the melanoma.

The terms "tumor" or "cancer" in an animal refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. "Tumor" includes both benign and malignant neoplasms. The term "neoplastic" refers to both benign and malignant atypical growth.

The term "melanocytic neoplasm" as used herein refers to an area of hyperpigmentation relative to the surrounding tissue. Melanocytic neoplasms include both nevi and primary melanoma as well as melanoma that has metastasized to anywhere in the body. Typcially, melanocytic neoplasms occur on skin, mucosal membranes, and the eye. Non-limiting exemplary melanocytic neoplasms can include melanoma, e.g., acral lentiginous melanoma, CSD melanoma, NCSD melanoma, lentigo maligna melanoma, muscosal melanoma, nodular melanoma, superficial spreading melanoma, desmoplastic melanoma, uveal melanoma, conjunctival melanoma, recurrent cellular blue nevi, melanoma arising in a congenital nevus, malignant blue nevus, and metastasis. Melanocytic neoplasms as used herein also include nevi. For example, non-limiting exemplary that are melanocytic neoplasms as used herein can include congenital nevus, congenital nevus with nodules, congenital nevus with desmoplastic reaction, giant congenital nevus with atypia, giant congenital nevus with nodules, congenital nevus without specific diagnosis, blue nevus, atypical blue nevus, atypical cellular blue nevus, blue nevus with neurocristic hamartoma, blue nevus without specific diagnosis and deep penetrating nevus without specific diagnosis.

The term "blue nevus" or "blue nevi" as used herein refers to an intradermal, i.e., within the dermal layer of the skin, melanocytic proliferation that exhibits increased pigmentation such that the nevus typically has a bluish color. A blue nevus, which can be congenital or acquired, may present in diverse ways ranging from discrete bluish moles (blue nevi) to large blue-gray patches affecting the conjunctiva and periorbital skin (nevus of Ota), shoulders (nevus of Ito), and the lower back (Mongolian spot).

"Biological sample" as used herein refers to a sample obtained from a patient suspected of having, or having a melanoma. In some embodiments, the sample may be a tissue biopsy, which refers to any type of biopsy, such as needle biopsy, fine needle biopsy, surgical biopsy, etc. The sample typically comprises a skin tissue sample harboring the neoplasm or suspected neoplasm, although the biological sample may also be derived from another, site, e.g., a site to which a melanoma may metastasize, or from the blood. In some cases, the biological sample may also be from a region adjacent to the neoplasm or suspected neoplasm.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, can also be used.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm nih gov/BLAST/ or the like). Such sequences are then said to be "substantially identical." This definition also refers to, or may be applied to, the complement of a test sequence. The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is 50-100 amino acids or nucleotides in length. For example, a nucleic acid probe that is used in the invention, may have at least 85%, typically 90%, or 95%, sequence identity to a contiguous region of SEQ ID NO:1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). For the purposes of this invention, BLAST and BLAST 2.0 are used with default parameters to determine percent sequence identity for the nucleic acids and proteins of the invention. Software for performing BLAST analyses is publicly available through the National Center for Biotechnology Information (NCBI). The BLASTN program (for nucleotide sequences) uses as defaults a wordlength (W) of 11, an expectation (E) of 10, a cutoff of 100, M=5, N=−4, and a comparison of both strands. For amino acid (protein) sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915)). For the purposes of this invention, the BLAST2.0 algorithm is used with the default parameters and the filter off.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequences.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y.S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference.

Other analogs include peptide nucleic acids (PNA) which are peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels may be incorporated into the KIT nucleic acids, proteins and antibodies at any position. Any method known in the art for conjugating the antibody to the label may be employed, e.g., using methods described in Hermanson, *Bioconjugate Techniques* 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not functionally interfere with hybridization. Thus, e.g., probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. Similarly, a "recombinant protein" is a protein made using recombinant techniques, i.e., through the expression of a recombinant nucleic acid as depicted above.

The phrase "selectively (or specifically) hybridizes to" refers to the binding, duplexing, or hybridizing of a molecule to a particular nucleotide sequence under stringent hybridization conditions when that sequence is present in a mixture (e.g., total cellular or library DNA or RNA, an amplification reaction), such that the binding of the molecule to the particular nucleotide sequence is determinative of the presence of the nucleotide sequence is the mixture.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

The phrase "functional effects" in the context of assays for testing compounds that inhibit activity of a Gnaq protein includes the determination of a parameter that is indirectly or directly under the influence of the Gnaq protein or nucleic acid, e.g., a functional, physical, or chemical effect, such as the ability to decrease tumorigenesis, or alter GTP hydrolase activity. Activities or functional effect of Gnaq can include protein-protein interaction activity, e.g., the ability of Gnaq to bind an antibody or other protein with which it interacts; GTP hydrolase activity, the ability of Gnaq to bind GTP and/or GDP; contact inhibition and density limitation of growth; cellular proliferation; cellular transformation; changes in pigmentation; growth factor or serum dependence; tumor specific marker levels; invasiveness into Matrigel; tumor growth and metastasis in vivo, including measurement of tumor growth and tumor "take" in a model system; mRNA and protein expression in cells, including those undergoing metastasis, and other characteristics of cancer cells. "Functional effects" include in vitro, in vivo, and ex vivo activities.

As used herein, "inhibitors" or "antagonists" of Gnaq (e.g. "Gnaq antagonists") refer to modulatory molecules or compounds that, e.g., bind to, partially or totally block activity, decrease, prevent, delay activation, inactivate, desensitize, or down regulate the activity or expression of Gnaq protein, phospholipase Cβ, or downstream molecules regulated by Gnaq, e.g., protein kinase C (PKC) Inhibitors can include siRNA or antisense RNA, genetically modified versions of Gnaq protein, e.g., versions with altered activity, as well as naturally occurring and synthetic Gnaq antagonists, antibodies, small chemical molecules and the like. Gnaq inhibitors for use in the invention are known in the art. For example, non-limiting exemplary inhibitors suitable for use with the present invention can include inhibitors of PKC, for example the relatively nonspecific PKC inhibitor staurosporine, the staurosporie analogue CPG41251, bryostatin-1, KAI-9803, 7-hydroxystaurosporine, L-threo-dihydrosphingosine (safingol), the non-selective PKC inhibitor (PKC412), ilmofosine (BM 41 440), indolcarbazole Gö6796 which is a more specific inhibitor of the classical PKC isoforms including PKCμ, the PKC-alpha antisense inhibitor LY900003, and the PKC-beta inhibitors LY333531, LY317615 (Enzastaurin). An exemplary antisense molecule suitable for use in depleting PKC-alpha mRNA is 5'-GTTCTCGCTGGTGAGTTTCA-3' (SEQ ID NO:3). Non-limiting exemplary inhibitors of phospholipase Cβ can include edelfosine and fluvirusin B[2]. Assays for identifying other inhibitors can be performed in vitro or in vivo, e.g., in cells, or cell membranes, by applying test inhibitor compounds, and then determining the functional effects on activity.

In some embodiments, samples or assays comprising Gnaq proteins that are treated with a potential inhibitor are compared to control samples without the inhibitor, to examine the effect on activity. Typically, control samples, e.g., melanoma cells, that have a Gnaq mutation and that are untreated with inhibitors are assigned a relative protein activity value of 100% Inhibition of Gnaq is achieved when the activity value relative to the control is changed at least 20%, preferably 50%, more preferably 75-100%, or more. In some embodiments, an inhibitor will activate a particular activity, such as GTP hydrolysis, however, the net effect will be a decrease in the activity of Gnaq, e.g., in comparison to controls that have activated Gnaq.

The phrase "changes in cell growth" refers to any change in cell growth and proliferation characteristics in vitro or in vivo, such as formation of foci, anchorage independence, semi-solid or soft agar growth, changes in contact inhibition and density limitation of growth, loss of growth factor or serum requirements, changes in cell morphology, gaining or losing immortalization, gaining or losing tumor specific markers, ability to form or suppress tumors when injected into suitable animal hosts, and/or immortalization of the cell. See, e.g., Freshney, *Culture of Animal Cells a Manual of Basic Technique* pp. 231-241 ($3^{rd}$ ed. 1994).

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). The term "antibody" also includes antigen binding forms of antibodies, including fragments with antigen-binding capability (e.g., Fab', F(ab')$_2$, Fab, Fv and rIgG. See also, Pierce Catalog and Handbook, 1994-1995 (Pierce Chemical Co., Rockford, Ill.). See also, e.g., Kuby, J., *Immunology*, $3^{rd}$ Ed., W.H. Freeman & Co., New York (1998). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol*:5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

An antibody immunologically reactive with a particular antigen can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

Typically, an immunoglobulin has a heavy and light chain Each heavy and light chain contains a constant region and a variable region, (the regions are also known as "domains"). Light and heavy chain variable regions contain four framework" regions interrupted by three hypervariable regions, also called complementarity-determining regions (CDRs).

References to "$V_H$" or a "VH" refer to the variable region of an immunoglobulin heavy chain of an antibody, including the heavy chain of an Fv, scFv, or Fab. References to "$V_L$" or a "VL" refer to the variable region of an immunoglobulin light chain, including the light chain of an Fv, scFv, dsFv or Fab.

A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule which contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332: 323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The term "fully human antibody" refers to an immunoglobulin comprising human hypervariable regions in addition to human framework and constant regions. Such antibodies can be produced using various techniques known in the art. For example in vitro methods involve use of recombinant libraries of human antibody fragments displayed on bacteriophage (e.g., McCafferty et al., 1990, *Nature* 348:552-554; Hoogenboom & Winter, J. Mol. Biol. 227:381 (1991); and Marks et al., *J. Mol. Biol.* 222:581 (1991)), yeast cells (Boder and Wittrup, 1997, *Nat Biotechnol* 15:553-557), or ribosomes (Hanes and Pluckthun, 1997, *Proc Natl Acad Sci USA* 94:4937-4942). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 6,150,584, 5,545,807; 5,545,806; 5,569,825; 5,625,126; 5,633,425; 5,661,016, and in the following scientific publications: (e.g., Jakobavits, *Adv Drug Dehv Rev.* 31:33-42 (1998), Marks et al., *Bio/Technology* 10:779-783 (1992); Lonberg et al., *Nature* 368:856-859 (1994); Morrison, *Nature* 368:812-13 (1994); Fishwild et al., Nature Biotechnology 14:845-51 (1996); Neuberger, *Nature Biotechnology* 14:826 (1996); Lonberg & Huszar, *Intern. Rev. Immunol.* 13:65-93 (1995).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance See, e.g., Epitope Mapping Protocols in Methods in Molecular Biology, Vol. 66, Glenn E. Morris, Ed (1996).

General Recombinant Methods

This invention relies in part on routine techniques in the field of recombinant genetics, e.g., for methods used in detecting Gnaq or for the preparation of Gnaq polypeptide that can be used in assays such as screening assays. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al., eds., 1994-1999). For example, in applications in which Gnaq, or a fragment thereof is to be produced, e.g., for use in an assay to detect inhibitors, routine expression protocols are employed.

Identification of a Gnaq Sequence in a Sample from a Patient

In one aspect of the invention, the presence of an activating mutation a Gnaq polynucleotide, e.g., mRNA or genomic DNA, or increased activity of a Gnaq protein and/or the presence of a sequence mutation in the Gnaq protein, is determined in biological samples suspected of comprising nevus and/or melanoma cells.

In some embodiments activating mutations in Gnaq mucleic acids are determined. As noted, human Gnaq sequences are well known. The Gnaq gene maps to 9q21 and the mRNA transcript is 2.188 kb, which encodes a 359 amino acid protein.

"Sequence mutation" as used in this application refers to changes in a polynucleotide sequence that result in changes to protein activity. Mutations can be nucleotide substitutions, such as single nucleotide substitutions, insertions, or deletions. Gnaq mutations in melanocytic neoplasms of the present invention are typically activating mutations that lead to constituitive activation of Gnaq activity. Without being bound to a theory, it is believed that the constituitive activity results from a lack of the GTP-hydrolase activity in the mutant Gnaq protein.

The current invention is based in part on the discovery of heterozygous somatic activating mutations present in Gnaq in melanocytic neoplasms, e.g., blue nevus, nevus of Ota, malignant blue nevus, uveal melanoma, and CSD melanomas (e.g., lentigo maligna melanoma). A mutation may be in any part of the Gnaq gene where the mutation leads to activation of Gnaq. A common sequence mutation site is present at Q209. Exemplary mutations that can be identified in the current invention are shown in Table 2. These mutations include CAA to CTA, and CAA to TTA (both of which result in a Q209L substitution), CAA to CCA which results in a Q209P substitution, CAA to CGA which results in a Q209R substitution, and CAA to TAT which results in a Q209Y substitution. As is understood in the art, the particular mutation is commonly referred to by the change in amino acid sequence that results from the mutation in the nucleic acid sequence.

In the present invention an altered level of Gnaq activity and/or a sequence mutation in Gnaq is detected for the diagnosis (or for prognostic indications) of melanocytic neoplasms, e.g., for the diagnosis of subtypes of melanoma such as uveal, acral, CSD, and malignant blue nevus, as well as benign blue nevus and nevus of Ota. Thus, biological samples obtained from patients that have or are suspected of having a melanocytic neoplasm can be analyzed for mutations in the sequence of Gnaq mRNA or protein. The presence of a mutation is conveniently analyzed using samples of RNA, DNA, or protein.

Detection of Sequence Mutations in Gnaq

In one embodiment, diagnostic and prognostic detection of a sequence mutation in Ganq is performed by determining the number of cells in a biological sample having a sequence mutation in Gnaq. Methods of evaluating the sequence of a particular gene are well known to those of skill in the art, and include, inter alia, hybridization and amplification based assays. A sequence mutation in Gnaq in the instant invention can be determined using a probe that selectively hybridizes to the mutant sequence.

In some embodiments, a Gnaq sequence mutation in a biological sample is determined by in situ hybridization, e.g., fluorescence in situ hybridization. In situ hybridization assays are well known (e.g., Angerer (1987) Meth. Enzymol 152: 649). The probes used in such applications specifically hybridize to the region of the Gnaq sequence harboring the mutation. Preferred probes are sufficiently long, e.g., from about 10, 15, or 20 nucleotides to about 50 or more nucleotides, so as to specifically hybridize with the target nucleic acid(s) under stringent conditions.

Any of a number of other hybridization-based assays can be used to detect a sequence mutation in Gnaq in the cells of a biological sample. For example, dot blots, array-based assays and the like can be used to determine Gnaq sequence mutations.

In some embodiments, amplification-based assays are used to detect sequence mutations in Gnaq or to measure the levels of Gnaq transcript. In such an assay, the Gnaq nucleic acid sequence acts as a template in an amplification reaction (e.g., Polymerase Chain Reaction, or PCR). Exemplary amplification-based assays can include RT-PCR methods well known to the skilled artisan (see, e.g., Ausubel et al., supra). Detailed protocols for PCR of DNA and RNA, including quantitative amplification methods,are known (see, e.g., Innis et al. (1990) PCR Protocols, A Guide to Methods and Applications, Academic Press, Inc. N.Y.; and Ausubel and Russell & Sambrook, both supra). The known nucleic acid sequences for Gnaq (see, e.g., SEQ ID NO:1) are sufficient to enable one of skill to routinely select primers to amplify any portion of the gene. Suitable primers for amplification of specific sequences can be designed using principles well known in the art (see, e.g., Dieffenfach & Dveksler, PCR Primer: A Laboratory Manual (1995)).

Other suitable amplification methods include, but are not limited to, ligase chain reaction (LCR) (see, Wu and Wallace (1989) Genomics 4: 560, Landegren et al. (1988) *Science* 241:1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

The presence of mutations in Gnaq DNA or RNA sequences can be determined using any technique known in the art. For example, in one embodiment, allele-specific oligonucleotide hybridization may be used, which relies on distinguishing a mutant from a normal nucleic acid sequence using an oligonucleotide that specifically hybridizes to the mutant or normal nucleic acid sequence. This method typically employs short oligonucleotides, e.g., 15-20 nucleotides, in length, that are designed to differentially hybridize to the normal or mutant allele. Guidance for designing such probes is available in the art. The presence of a mutant allele is determined by measuring the amount of allele-specific oligonucleotide that hybridizes to the sample Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099.

In other embodiments, the presence (or amount) of a normal or mutant Gnaq nucleic acid can be detected using allele-specific amplification or primer extension methods. These reactions typically involve use of primers that are designed to specifically target a normal or mutant allele via a mismatch at the 3' end of a primer. The presence of a mismatch effects the ability of a polymerase to extend a primer when the polymerase lacks error-correcting activity. The amount of amplified product can be determined using a probe or by directly measuring the amount of DNA present in the reaction.

Detection of levels of Gnaq nucleic acids, e.g., levels of normal and/or mutant Gnaq polynucleotides, or the presence of a Gnaq mutation can also be performed using a quantitative assay such as a 5'-nuclease activity (also referred to as a "TaqMan®" assay), e.g., as described in U.S. Pat. Nos. 5,210, 015; 5,487,972; and 5,804,375; and Holland et al., 1988, Proc. Natl. Acad. Sci. USA 88:7276-7280. In such an assay, labeled detection probes that hybridize within the amplified region are added during the amplification reaction. In some embodiments, the hybridization probe can be an allele-specific probe that discriminates a normal or mutant allele. Alternatively, the method can be performed using an allele-specific primer and a labeled probe that binds to amplified product. In other embodiments, the probe may not discriminate between a mutant and normal allele.

In other embodiments, the presence of a mutant Gnaq allele can be conveniently determined using DNA sequencing, such as pyrosequenceing, or other known sequencing techniques. Other detection methods include single-stranded conformational polymorphism or restriction fragment length polymorphism detection methods and denaturing gradient gel electrophoresis analysis.

As indicated above, in some embodiments, levels of Gnaq RNA are detected. Methods of detecting and/or quantifying the level of Gnaq gene transcripts (mRNA or cDNA made therefrom) using nucleic acid hybridization techniques are known to those of skill in the art. For example, expression levels of Gnaq can also be analyzed by techniques such as RT-PCR, e.g., using real-time RT-PCR using allele-specific primers or probes, dot blotting, in situ hybridization, RNase protection, probing DNA microchip arrays, and the like.

Overexpression of Gnaq, either mutated sequences or normal nucleic acid and/or polypeptide sequences, can be detected, e.g., using quantitative sequences known in the art such as those described hereinabove. Overexpression is determined with reference to a control, e.g, a normal tissue or normal melanocytes.

Detection of Gnaq Polypeptide Sequences

Altered Gnaq expression and/or activity can also be detected by detecting Gnaq protein or activity. For example, detection of Gnaq protein activity or the presence of Gnaq proteins that have a mutation, can be used for diagnostic purposes or in screening assays. In some embodiments, the level of Gnaq or the presence of a normal or mutant Gnaq polypeptide in a sample is conveniently determined using immunological assays. In other embodiments, Gnaq activity can be used to determine the presence of activating mutation of Gnaq in a biological sample. The following section discusses immunological detection of Gnaq. The section also relates to generation and engineering of antibodies that can be used, e.g., in therapeutic applications.

Immunological Detection Gnaq

Antibodies can be used to detect Gnaq or can be assessed in the methods of the invention for the ability to inhibit Gnaq. The detection and/or quantification of Gnaq can be accomplished using any of a number of well recognized immunological binding assays. A general overview of the applicable technology can be found in Harlow & Lane, Antibodies: A Laboratory Manual (1988) and Harlow & Lane, Using Antibodies (1999). Other resources include see also Methods in Cell Biology: Antibodies in Cell Biology, volume 37 (Asai, ed. 1993); Basic and Clinical Immunology (Stites & Ten, eds., 7th ed. 1991, and Current Protocols in Immunology (Coligan, et al. Eds, John C. Wiley, 1999-present). Immunological binding assays can use either polyclonal or monoclonal antibodies. In some embodiments, antibodies that specifically detect mutant Gnaq molecules may be employed.

Commonly used assays include noncompetitive assays (e.g., sandwich assays) and competitive assays. In competitive assays, the amount of Gnaq present in the sample is measured indirectly by measuring the amount of a known, added (exogenous) Gnaq displaced (competed away) from an anti-Gnaq antibody by the unknown Gnaq present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers, which are then detected according to standard techniques (see Monroe et al., Amer. Clin. Prod. Rev. 5:34-41 (1986)).

Immunoassays also often use a labeling agent to specifically bind to and label the complex formed by the antibody and antigen. The labeling agent may itself be one of the moieties comprising the antibody/antigen complex. Thus, the labeling agent may be a labeled Gnaq polypeptide or a labeled anti-Gnaq antibody. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. The labeling agent can be modified with a detectable moiety, such as biotin, to which another molecule can specifically bind, such as streptavidin. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent compounds (e.g., fluorescein isothiocyanate, Texas red, rhodamine, fluorescein, and the like), radiolabels, enzymes (e.g., horse radish peroxidase, alkaline phosphatase and others commonly used in an ELISA), streptavidin/biotin, and colorimetric labels such as colloidal gold or colored glass or plastic beads (e.g., polystyrene, polypropylene, latex, etc.). Chemiluminescent compounds may also be used. For a review of various labeling or signal producing systems that may be used, see U.S. Pat. No. 4,391,904.

Antibodies to Gnaq are commercially available (e.g., Genesis Biotech, Inc. Taipei County, Taiwan). In some embodiments, mutations to Gnaq can be detected using antibodies that specifically bind a mutant form, thus immunoassays can also be used to detect mutant Gnaq proteins.

Gnaq or a fragment thereof, e.g., the portion of the peptide frequently containing a sequence mutation, may be used to produce antibodies specifically reactive with Gnaq. For example, a recombinant Gnaq or an antigenic fragment thereof, is isolated. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure form. The product is then used to generate antibodies.

Methods of producing polyclonal and monoclonal antibodies that react specifically with Gnaq are known to those of skill in the art (see, e.g., Coligan; Harlow & Lane, both supra). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)). Such antibodies can be used for diagnostic or prognostic applications, e.g., in the detection of melanomas or for other cancers that exhibit increased expression or activity of Gnaq.

Typically, polyclonal antisera with a titer of $10^4$ or greater are selected and tested for cross reactivity against non-Gnaq proteins or even other related proteins from other organisms, using a competitive binding immunoassay. Specific polyclonal antisera and monoclonal antibodies will usually bind with a Kd of at least about 0.1 mM, more usually at least about 1 µM, optionally at least about 0.1 µM or better, and optionally 0.01 µM or better.

In some embodiments, a Gnaq antibody may be used for therapeutic applications. For example, in some embodiments, such an antibody may used to reduce or eliminate a biological function of Gnaq as is described below. That is, the addition of anti-Gnaq antibodies (either polyclonal or preferably monoclonal) to a melanocytic neoplasm (or a cell population containing cancererous cells) may reduce or eliminate the neoplasm. Generally, at least a 25% decrease in activity, growth, size or the like is preferred, with at least about 50% being particularly preferred and about a 95-100% decrease being especially preferred.

Often, the antibodies to the Gnaq proteins for therapeutic applications are humanized antibodies (e.g., Xenerex Biosciences, Mederex, Inc., Abgenix, Inc., Protein Design Labs, Inc.). Human antibodies can also be produced using various techniques known in the art, including phage display libraries (Hoogenboom & Winter, J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, p. 77 (1985) and Boerner et al., J. Immunol. 147(1):86-95 (1991)). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg & Huszar, Intern. Rev. Immunol. 13:65-93 (1995).

Detection of Activity

As appreciated by one of skill in the art, Gnaq activity can be detected to evaluate expression levels or for identifying inhibitors of activity. The activity can be assessed using a variety of in vitro and in vivo assays, including GTP and GDP binding activity, GTP-hydrolase activity, or measurement of phospholipase Cβ. In some embodiments Gnaq activity can be evaluated using additional endpoints, such as those associated with transformation or pigmentation. Such assays are described in greater detail in the examples and section detailing methods of identifying additional Gnaq inhibitors. Typically Gnaq activity is determined by measuring the ability to bind a protein to which it interacts, e.g., an antibody, ligand, or other protein, such as signaling molecules.

Disease Diagnosis/Prognosis

Gnaq nucleic acid and polypeptide sequences can be used for diagnosis or prognosis of a melanocytic neoplasm in a patient. For example, as described above, the sequence, level, or activity of Gnaq in a melanocytic neoplasm sample from a patient can be determined, wherein an alteration, e.g., an increase in the level of expression or activity of Gnaq or a sequence mutation in Gnaq, indicates the presence or the likelihood of a melanocytic neoplasm.

The methods of the present invention can be used to determine the optimal course of treatment in a patient with cancer. For example, the presence of a sequence mutation in Gnaq can indicate that certain therapeutics, such as those that target Gnaq, phospholipase Cβ, or downstream pathways regulated by Gnaq will be beneficial to those patients. In addition, a correlation can be readily established between the presence of a defect or sequence mutation in Gnaq, and the relative efficacy of one or another anti-melanoma agent. Such analyses can be performed, e.g., retrospectively, i.e., by analyzing for a Gnaq defect or sequence mutation in samples taken previously from patients that have subsequently undergone one or more types of anti-cancer therapy, e.g., therapies that target G-proteins or phospholipase Cβ, or other downstream pathways regulated by Gnaq and correlating the presence of the defect with the known efficacy of the treatment.

Often, such methods will be used in conjunction with additional diagnostic methods, e.g., detection of other melanoma indicators, e.g., cell morphology, and the like. In other embodiments, a tissue sample known to contain melanoma cells, e.g., from a tumor, will be analyzed for Gnaq defects to determine information about the cancer, e.g., the efficacy of certain treatments, such as therapeutics that target Gnaq, or downstream pathways regulated by Gnaq.

In some embodiments, analysis of melanoma cells for the presence of Gnaq defects or sequence mutation can be used to determine the prognosis of a patient with melanoma or for determining progression of the disease. A "diagnostic presence" can be increased levels of Gnaq mRNA or protein and/or activity, and/or the presence of sequence mutations in Gnaq that alter function.

Any biological sample suspected of containing melanoma cells can be evaluated to determine progression. For example, tissues from visceral organs, blood, lymph nodes and the like can be analyzed for the presence of Gnaq sequence mutations and or increased levels of Gnaq activity.

Screening for Inhibitors or Modulators of Gnaq

In another aspect, this invention includes methods of treating melanoma that overexpress and/or have a mutation in Gnaq where the method comprises administering an inhibitor or Gnaq antagonist. Inhibitors and Gnaq antagonists are known. For example, non-limiting exemplary inhibitors suitable for use with the present invention can include specific and nonspecific inhibitors of PKC and various PKC isoforms including PKCµ and PKCε. Exemplary non-limiting inhibitors suitable for use with the present incvention include staurosporine, the staurosporine analogue CPG41251, bryostatin-1, KAI-9803, 7-hydroxystaurosporine, L-threo-dihydrosphingosine (safingol), the non-selective PKC inhibitor (PKC412), ilmofosine (BM 41 440), Gö6976, which is an indolcarbazole that more specifically inhibits the classical isoforms of PKC, including PCKµ, the PKC-alpha antisense inhibitor LY900003, and the PKC-beta inhibitors LY333531, LY317615 (Enzastaurin). Non-limiting exemplary inhibitors of phospholipase Cβ can include edelfosine and fluvirusin B[2], which are also suitable for use in the present invention.

Other inhibitors include inhibitors such as antibodies, peptide, nucleic acids and the like. As used herein, a Gnaq inhibitor can be a molecule that modulates Gnaq nucleic acid expression and/or Gnaq protein activity, or downstream pathways regulated by Gnaq. For example, a non-limiting exemplary antisense molecule suitable for use in depleting PKC-alpha mRNA is 5'-GTTCTCGCTGGTGAGTTTCA-3' (SEQ ID NO:3).

Method of screening for modulators of compounds can employ, for example, melanoma cells in which Gnaq is overexpressed or mutated. Such modulators may be candidate Gnaq GTP hydrolase modulators.

Additional Gnaq inhibitors can be identified by assaying for Gnaq activity, e.g., GTP binding or GTP hydrolase activity. Such assays employ known Gnaq sequences or fragments, e.g, the guanine binding domain of Gnaq, or variants thereof. An exemplary human Gnaq polypeptide sequence that could be used in such assays is provided in SEQ ID NO:2.

Activity assays are used to identify inhibitors that can be used as therapeutic agents, e.g., antibodies to Gnaq and antagonists of Gnaq activity Inhibitors of Gnaq activity are tested using Gnaq polypeptides, either recombinant or naturally occurring. The protein can be isolated, expressed in a cell, expressed in tissue or in an animal, either recombinant or naturally occurring. For example, transformed cells can be used. Modulation is tested using one of the in vitro or in vivo assays described herein. Activity can also be examined in vitro with soluble or solid state reactions, using a Gnaq fragment that binds to another protein, e.g, phospholipase Cβ, or GTP.

In another embodiment, mRNA and/or protein expression levels can be measured to assess the effects of a test compound on Gnaq expression levels. A host cell expressing Gnaq is contacted with a test compound for a sufficient time to effect any interactions, and then the level of mRNA or protein is measured. The amount of time to effect such interactions may be empirically determined, such as by running a time course and measuring the level of expression as a function of time. The amount of expression may be measured by using any method known to those of skill in the art to be suitable.

The amount of expression is then compared to the amount of expression in the absence of the test compound. A substantially identical cell may be derived from the same cells from which the recombinant cell was prepared but which had not been modified by introduction of heterologous DNA. A difference in the amount of expression indicates that the test compound has in some manner altered Gnaq levels.

In some assays to identify Gnaq inhibitors, samples that are treated with a potential inhibitor are compared to control samples to determine the extent of modulation. Control samples without the mutation and untreated with candidate inhibitors are assigned a relative activity value of 100 Inhibition of Gnaq is achieved when the activity value relative to the control is about 80%, optionally 50%, optionally 25-0%.

The compounds tested as inhibitors of Gnaq can be any small chemical compound, or a biological entity, e.g., a macromolecule such as a protein, sugar, nucleic acid or lipid. Alternatively, modulators can be genetically altered versions of Gnaq. Typically, test compounds will be small chemical molecules and peptides or antibodies.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a Log P over 5 (or M Log P over 4.15); and/or having more than 10 H-bond acceptors (expressed as the sum of Ns and Os). See, e.g., Lipinski et al. *Adv Drug Delivery Res* 23:3-25 (1997). Compound classes that are substrates for biological transporters are typically exceptions to the rule.

Essentially any chemical compound can be used as a potential modulator or ligand in the assays of the invention. Most often, compounds can be dissolved in aqueous or organic (especially DMSO-based) solutions. The assays are designed to screen large chemical libraries by automating the assay steps, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Expression Assays

Certain screening methods involve screening for a compound that modulates the expression of Gnaq. Such methods generally involve conducting cell-based assays in which test compounds are contacted with one or more cells expressing Gnaq and then detecting a decrease in expression (either transcript or translation product).

Expression can be detected in a number of different ways. As described herein, the expression levels of the protein in a cell can be determined by probing the mRNA expressed in a cell with a probe that specifically hybridizes with a Gnaq transcript (or complementary nucleic acid derived therefrom). Alternatively, protein can be detected using immunological methods in which a cell lysate is probed with antibodies that specifically bind to the protein.

Other cell-based assays are reporter assays conducted with cells that do not express the protein. Often, these assays are conducted with a heterologous nucleic acid construct that includes a promoter that is operably linked to a reporter gene that encodes a detectable product.

Melanoma Treatment and Administration of Pharmaceutical and Vaccine Compositions Inhibitors of Gnaq can be administered to a patient for the treatment of a melanocytic neoplasm having a sequence mutation in Gnaq. As described in detail below, the inhibitors are administered in any suitable manner, optionally with pharmaceutically acceptable carriers. In some embodiments, inhibitors of PKC or phospholipase Cβ are administered. Protocols for the administration of inhibitors are known and can be further optimized for melanoma patients based on principles known in the pharmacological arts (*Remington's Pharmaceutical Sciences*, 17th ed., 1989).

The inhibitors can be administered to a patient at therapeutically effective doses to prevent, treat, or control a melanocytic neoplasm. The compounds are administered to a patient in an amount sufficient to elicit an effective protective or therapeutic response in the patient. An effective therapeutic response is a response that at least partially arrests or slows the symptoms or complications of the disease. An amount adequate to accomplish this is defined as "therapeutically effective dose." The dose will be determined by the efficacy of the particular Gnaq inhibitor employed and the condition of the subject, as well as the body weight or surface area of the area to be treated. The size of the dose also will be determined by the existence, nature, and extent of any adverse effects that accompany the administration of a particular compound in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Kits for Use in Diagnostic and/or Prognostic Applications

The invention also provides kits for diagnostic or therapeutic applications. For diagnostic/prognostic applications, such kits may include any or all of the following: assay reagents, buffers, Gnaq probes, primers, antibodies, or the like In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Example 1

Examination of Melanoma and Nevus Samples for Presence of Gnaq Sequence Mutation To determine whether Gnaq plays a role in human melanocytic neoplasia, the coding regions of Gnaq were sequenced in a broad spectrum of benign and malignant melanocytic tumors. As a control, the Gnaq coding region was also sequenced in normal surrounding tissue from selected biopsies.

Biological Samples

DNA from melanoma and nevi samples was obtained from previous studies (see, Curtin, J. A., et at., (2005) *N Engl J Med*, 353(20):2135-47) or was obtained from archival, paraffin-embedded biopsies from collections in San Francisco and Germany, under the approval of the institutional review boards at UCSF and Stanford. All of these samples contained some lesional tissue isolated from the dermis, since lesions located only in the epidermis did not provide sufficient DNA for analysis.

Sequencing

DNA was extracted from paraffin blocks as previously described. See, Bastian, et al., (1998) *Cancer Res*. 58(10): 2170-2175. Sample DNA was amplified using PCR, purified using PCR purification columns and then used as templates for sequencing reactions, which were done in both directions. Samples identified with mutations in both sequencing directions were replicated at least twice and verified with restriction fragment length polymorphism (RFLP) assays. The reaction conditions for sequencing were 0.25 mM each dNTPs, 0.4×BSA (New England Biolabs), 1 U Hotstar Taq (Qiagen), 1X Hotstar Taq buffer (Qiagen), and 0.5 uM each primer, 5'-cccacaccctactttctatcatttac-3' (SEQ ID NO:4) and 5'-ttttccctaagtttgtaagtagtgc-3' (SEQ ID NO:5) (for GNAQ exon 5.) Other primer sequences for GNAQ and GNA11 are available on request. PCR consisted of 35 cycles of 95 degrees (30 seconds), 58 degrees (1 minute), and 72 degrees (1 minute). PCR reactions were purified using columns and then used as templates for sequencing reactions using Big Dye (ABI), which were done in both directions. Samples identified with mutations in both sequencing directions were replicated at least twice. Mutations 1-3 (Table 2) were verified with a RFLP assay. Mutations 1 and 2 create an Eco0109I restriction site, while mutation 3 (if both altered base pairs are in the same allele) produces an AflII restriction site. Accordingly, samples showing mutation 3 by sequencing analysis could be cut with AflII, proving that the tandem base pair alteration is within a single allele.

Sensitive Assay for Detecting Q209 Mutations in Mixed Cell Populations

The peptide nucleic acid (PNA), Ac-tctctgacctttggc-CONH$_2$ (SEQ ID NO:6), was resuspended in 50% DMF and used at a final concentration of 4 uM against 2 ng template DNA in a 25 ul reaction. The reaction conditions were 0.25 mM dNTPs, 6X BSA, 2 U Hotstar Taq, 1X Hotstar Taq buffer, and 0.5 uM each primer, 5'-ttttccctaagtttgtaagtagtgc-3' (SEQ ID NO:5); and 5'-atccattttcttctctctgacc-3' (SEQ ID NO:7). PCR consisted of 40 cycles of 95 degrees (1 mM), 73 degrees (1 min), 57 degrees (45 sec), and 72 degrees (1 min). To confirm that the samples contained the mutant allele, samples were digested with AflII and Eco0109I, which do not cut the wildtype sequence.

Results

Heterozygous, somatic substitution mutations of Q209 in Gnaq were found in 83% of blue nevi representing different histopathological growth patterns (Table 1, Table 2). The high prevalence of somatic, constitutive active mutations in Gnaq in blue nevi together with the previous observation that germline hypermorphic Gnaq alleles lead to intradermal hyperpigmentation in the mouse (Van Raamsdonk et al. (2004)) suggests that this is the major pathway for forming these types of lesions. Although rare, blue nevi can give rise to malignant melanoma, which is referred to as a "malignant blue nevus". A Gnaq-Q209 mutation was found in 1 of 2 "malignant blue nevi" samples analyzed (Table 1, Table 2).

Uveal melanoma biopsies also showed mutations in Gnaq-Q209 in 22 of 48 samples (46%) having a somatic (not present in the surrounding normal tissue), heterozygous mutation to either leucine or proline (Table 1, Table 2), indicating that Gnaq plays a pivotal role in uveal melanoma formation.

Each of the five Gnaq mutations detected in melanoma and nevi samples predict a non-synonymous substitution for glutamine 209 to leucine (66%) proline (30%) arginine (2%) or tyrosine (2%) as shown in Table 2. Each of these mutations was confirmed using a RFLP assay (data not shown).

TABLE 1

The frequency of Gnaq mutations in melanoma and nevi biopsy samples.

| | Diagnosis | % Mutant | N |
|---|---|---|---|
| Cutaneous and mucosal melanomas | Melanoma on skin without chronic sun-induced damage (non-CSD) | 0% | 15 |
| | Melanoma on skin with chronic sun-induced damage (CSD) | 4% | 27 |
| | Acral melanoma | 0% | 15 |
| | Mucosal melanoma | 0% | 14 |
| | "Malignant blue nevus" | 50% | 2 |
| | Melanoma arising in congenital nevus | 0% | 3 |
| | Spitzoid melanoma | 0% | 2 |
| | Total | | 78 |
| Nevi | Blue nevus | 83% | 29 |
| | Nevus of Ota | 6% | 17 |

TABLE 1-continued

The frequency of Gnaq mutations in melanoma and nevi biopsy samples.

|  | Diagnosis | % Mutant | N |
|---|---|---|---|
|  | Congenital nevus | 0% | 7 |
|  | Deep penetrating nevus | 0% | 16 |
|  | Proliferating nodule in giant congenital nevus | 0% | 7 |
|  | Spitz nevus | 0% | 8 |
|  | Total |  | 84 |
| Ocular melanomas | Uveal melanoma | 46% | 48 |
|  | Uveal melanoma cell line | 27% | 15 |
|  | Conjunctival melanoma | 0% | 11 |
|  | Total |  | 74 |
|  | Grand Total |  | 236 |

TABLE 2

Three Gnaq mutations at codon 209 in melanoma and nevi samples.

| Diagnosis | Number of samples with mutation ||||| 
|---|---|---|---|---|---|
|  | 1: CAA(Q) to CTA(L) | 2: CAA(Q) to CCA(P) | 3: CAA(Q) to TTA(L) | 4: CAA(Q) to CGA (R) | 5. CAA(Q) to TAT(Y) |
| CSD Melanoma | 1 | 0 | 0 | 0 | 0 |
| "Malignant blue nevus" | 1 | 0 | 0 | 0 | 0 |
| Blue nevus | 17 | 4 | 4 | 0 | 0 |
| Uveal melanoma | 10 | 10 | 0 | 1 | 1 |
| Uveal melanoma cell lines | 2 | 2 | 0 | 0 | 0 |
| Total | 31 (58%) | 16 (30%) | 4 (8%) | 1 (2%) | 1 (2%) |

Example 2

GNAQ that has a Q209L Mutation Transforms Melanocytes

To assess the effect of GNAQ$^{Q209L}$ on human melanocytes, we established epitope-tagged lentiviral expression constructs to transfect normal and genetically modified human melanocytes, the latter of which have an extended life span, but still require additional factors (cAMP, TPA) for growth (hTERT/CDK4$^{R24C}$/p53$^{DD}$ melanocytes). See, Garraway, L. A. et al., *Nature* 436(7047):117 (2005). Stable transfection of GNAQ$^{Q209L}$ into primary human melanocytes was insufficient to induce anchorage independent growth (data not shown). In contrast, transfection of GNAQ$^{Q209L}$ into hTERT/CDK4$^{R24C}$/p53$^{DD}$ melanocytes resulted in anchorage independent growth with efficiencies comparable or slightly greater than transfection with NRAS$^{Q61R}$ (FIG. 1a-b). Furthermore, GNAQ$^{Q209L}$ induced a highly transformed morphology in melanocytes (FIG. 1c).

Plasmids

A plasmid with the entire GNAQ coding region of GNAQ$^{Q209L}$ was obtained from UMR cDNA Resource Center. The wild-type counterpart was generated by site-specific mutagenesis of codon 209. The coding regions of both constructs were epitope-tagged with an N-terminal Flag-tag and cloned into the lentiviral expression vector FG12. All constructs were sequenced for confirmation.

Cell Culture hTERT/CDK4$^{R24C}$/p53$^{DD}$ melanocytes were a gift from Dr. David Fisher, Dana Farber Cancer Institute and are human melanocytes in which the p53 and p16/CDK4/retinoblastoma protein pathways are inactivated in conjunction with telomerase (hTERT) expression. hTERT/CDK4$^{R24C}$/p53$^{DD}$ melanocytes were cultured in glutamine containing Ham's F12 supplemented with 7% FBS, 50 ng/ml TPA, 0.1 mM IBMX, 10 µM Na$_3$VO$_4$, 1 mM dbcAMP. Primary normal melanocytes were a gift from Dr. Meenhard Herlyn, Wistar Institute, and were cultured in MCDB153 supplemented 20% FBS, 2% chelated FBS, 5 µg/ml L-glutamin, 15 µg/ml cholera toxin, 0.5 ng/ml bFGF, 100 nM ET3 and 1.68 mM SCF. Cell lines Mel202 and 293T were cultured in RPMI supplemented with 10% fetal bovine serum.

Lentiviral Infection

Viral supernatant were generated using 293T cells transfected with 10 µg plasmid and appropriate lentiviral packaging plasmids. Media was changed 16 hr after transfection and the virus was harvested 40 to 56 hr later. Human primary and immortalized melanocytes were infected and infection efficiencies were estimated by the percent of GFP expressing cells.

Transient Infection 293T cells were seeded in 6-well plates at 1×10$^6$ cells per well with RPMI/10% FCS. Transfections were carried out using Lipofectamine 2000 (Invitrogen) and 2 µg plasmid pcDNA™ 6.2/V5-DEST® Gateway vector (Invitrogen) alone or containing the complete coding region for either GNAQ$^{Q209L}$ or GNAQ$^{WT}$, respectively. Cells were lysed 48 hour post-transfection and assayed for protein content.

Cell Proliferation Assay.

Relative cell numbers were quantified by the CyQUANT® Cell (Invitrogen) Proliferation Assay Kit according to the manufacturer's protocol using 96-well plates. 7.5×10$^3$ Mel202 cells were left untreated or were transfected with either non-targeting siRNA, GNAQ siRNA, 20 µM MEK inhibitor U0126 (Promega) and the fluorescent intensity read after 72 h. Cells with mock transfection and treatment with DMSO were used as controls.

Example 3

Figures 2A, 2B:
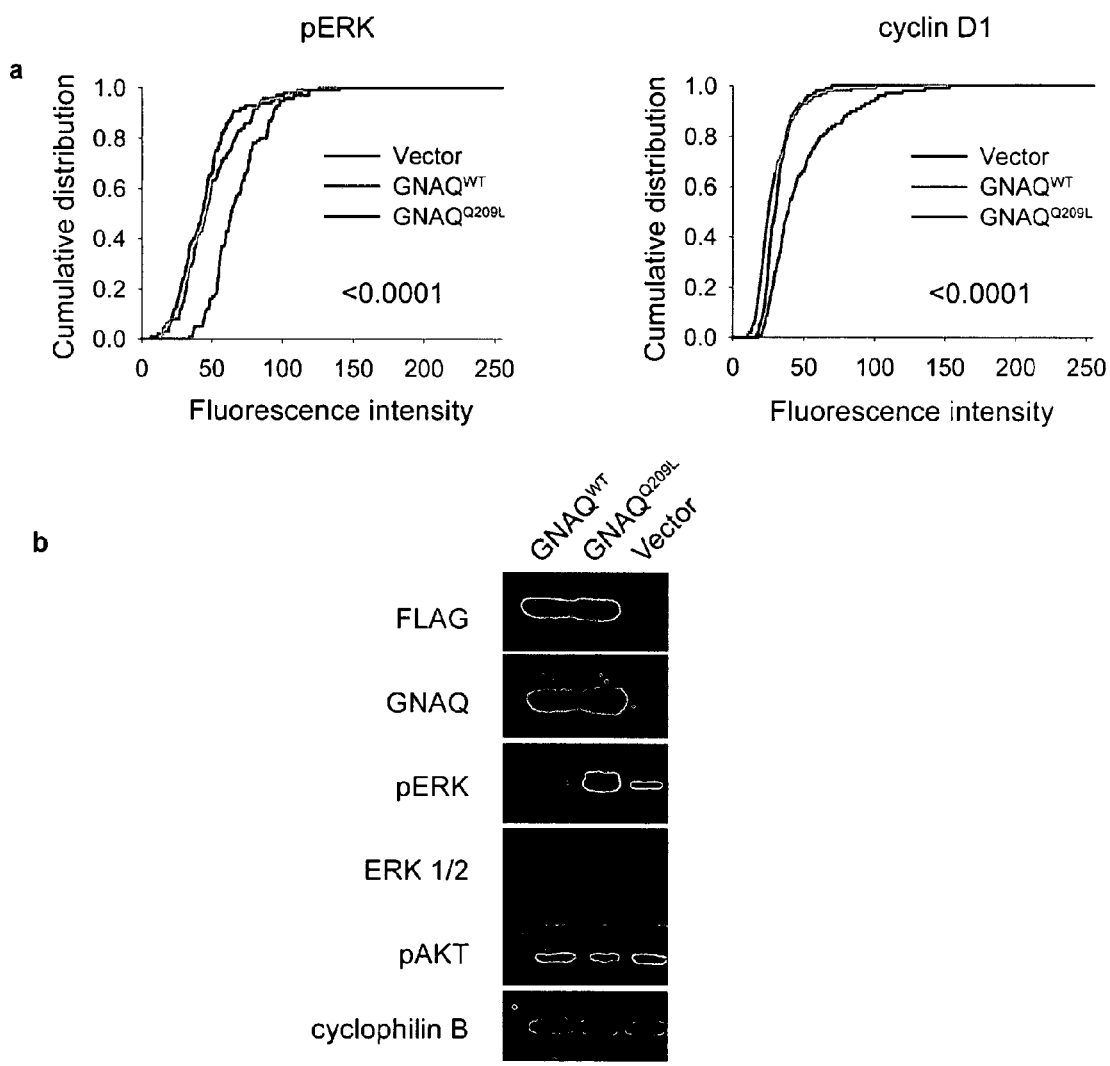
FIG. 2a-2b provides exemplary data showing that GNAQ$^{Q209L}$ induces MAP kinase activation in human melanocytes. a, hTERT/CDK4R24C/p53DD melanocytes express increased levels of pERK and cyclin D1 after stable transfection with GNAQ$^{Q209L}$ compared to GNAQ$^{WT}$ or vector only; cumulative distribution of mean pixel fluorescence intensity per cell (p-values: GNAQ$^{Q209L}$ vs. vector control). b, Western blot showing increased pERK but not pAKT levels in 293 cells expressing Flag-tagged GNAQ$^{Q209L}$ compared to cells transfected with GNAQWT or vector control. Cyclophilin B is shown as a loading control.

GNAQQ209L Contributes to MAP-Kinase Pathway Activation in Human Melanocytes and Uveal Melanoma Cells Signaling pathways downstream of GNAQ include activation of protein kinase C family members via the release of diacylglycerol (DAG) by phospholipase Cβ. Consistently, GNAQ$^{Q209L}$-transformed melanocytes grew in soft agar in the absence of TPA, a synthetic DAG analog (FIG. 1a-b). PKC activation by way of GNAQ activation can activate the MAP-kinase pathway in other cell types (see, Hubbard, K. B. and Hepler, J. R., *Cell Signal* 18 (2):135 (2006); Goldsmith, Z. G. and Dhanasekaran, D. N., *Oncogene* 26 (22):3122 (2007)). Uveal melanomas display MAP-kinase activation (see, Zuidervaart, W. et al., *Br J Cancer* 92 (11):2032 (2005)), but none of the uveal melanomas in our study showed mutations in BRAF or NRAS, consistent with other studies (see, e.g., Saldanha, G. et al., *Int J Cancer* 111 (5), 705 (2004); Cruz, F., 3rd et al., *Cancer Res* 63 (18):5761 (2003)). We therefore tested whether GNAQ$^{Q209L}$ would contribute to MAP-kinase pathway activation in human melanocytes and uveal melanoma cells. As shown in FIGS. 2a and b, GNAQ$^{Q209L}$ transfection into hTERT/CDK4$^{R24C}$/p53$^{DD}$ melanocytes caused increased levels of phospho-ERK and cyclin D1 expression compared to control cells transfected with wildtype GNAQ (GNAQ$^{WT}$) or an empty vector (Vector). Similar results were obtained with GNAQ$^{Q209L}$ transfection into primary human melanocytes and 293T cells.

Figures 3A, 3B, 3C:
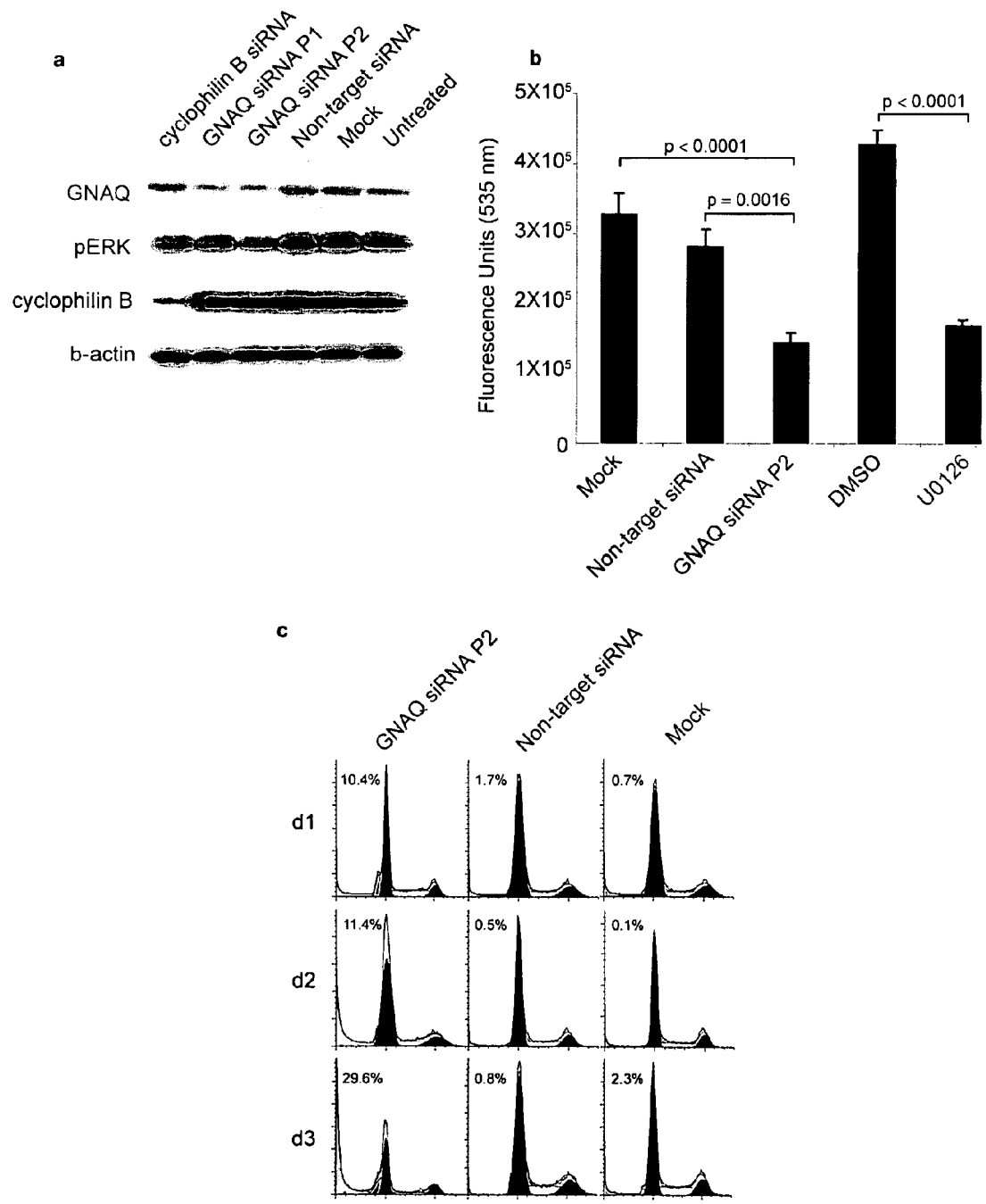
FIG. 3a-3c shows siRNA mediated knock-down of GNAQ in uveal melanoma cell line, Mel202. a, shows decreased levels of phospho-ERK in response to siRNA. b, shows a decrease in cell number in response to GNAQ siRNA, and c, shows an increase in apoptosis of the Mel202 cells compred to control cells in response to GNAQ siRNA.

Uveal melanoma cells were also subjected to treatment with siRNA that targets GNAQ. The results show that siRNA-mediated knock-down of GNAQ in the uveal melanoma cell line, Mel202, which harbors the GNAQ-Q$^{209L}$ mutation, resulted in a decrease of phospho-ERK levels (FIG. 3a). In addition, GNAQ knock-down in Mel202 cells causes both a substantial decrease in cell number (FIG. 3b) and a marked increase in apoptosis as compared to control cells (FIG. 3c). High levels of phospho-PKCµ in GNAQ mutant melanoma cells were also dramatically reduced upon treatment with two different pools of GNAQ siRNAs, whereas levels of phospho-PKCα/βII remained unaffected. The data therefore implicate PKCµ as playing a role in uveal melanoma. Data from a transgenic mouse model also implicates PKCε (10).

Immunofluorescence

Human primary and hTERT/CDK4$^{R24C}$/p53$^{DD}$ melanocytes were cultured on cover slips in 6 well plates and infected with lentiviral vectors containing either GNAQ$^{Q209L}$ GNAQ$^{WT}$, or an empty vector as control. Five days after infection, cells were fixed with 4% formaldehyde in PBS for 10 min at room temperature, permeabilized with 0.2% Triton X100 in PBS for 10 min at room temperature and incubated with 3% bovine serum albumin for 10 min at room temperature as a blocking step. Antibodies against pERK (E-4, Santa Cruz Biotechnology), cyclin D1 (M-20, Santa Cruz Biotechnology) and GNAQ (C-19, Santa Cruz biotechnology) were detected using secondary antibodies labeled with Alexa Fluor 594 and 532 (Molecular Probes). Images were taken at fixed exposures with an Axio Image M1 microscope (Zeiss, Germany) equipped with a gray scale M4$^+$CL camera and Isis software (Metasystems, Germany). The fluorescence intensities of individual cells were quantified using ImageJ software and the mean pixel intensities were used for statistical analysis using Microsoft Excel and Data Desk.

Soft Agar Assay

Human primary melanocytes (10×10$^4$) and hTERT/CDK4$^{R24C}$/p53$^{DD}$ melanocytes stably expressing GNAQ$^{Q209L}$, GNAQ$^{WT}$, NRAS$^{Q61R}$ stably expressing GNA or vector control were suspended in full media containing 0.35% agar and plated on a lower layer of 0.5% agar in 6 well plates. After 28 days, cells were stained with 0.005% crystal violet. Images from colonies were captured using a flatbed scanner at 600 dpi. Colony number and size were quantified using ImageJ software.

Cell Cycle Analysis

Mel202 cells transfected with siRNA were trypsinized, washed with cold PBS and fixed with 70% ethanol Fixed cells were stained with propidium iodide in RNase staining buffer (BD Pharmingen). Cell cycle measurements were performed on a FACSCalibur (BD Biosciences), with minimum of 20.000 events, and profiles were analyzed using FlowJo and ModFit.

siRNA Transfection.

Mel202 were plated in RPMI/10% FCS in 6 well or 96 well plates at 1.5×10$^5$ or 5×10$^3$ cells per well, respectively. Two different pools; each comprised of four siRNA duplexes (Dharmacon) (pool 1: 5'-CAAUAAGGCUCAUGCA-CAAUU-3' (SEQ ID NO:8), 5'-CGACGAGAAUAUCAA-UUAUUU-3' (SEQ ID NO:9), 5'-GCAAGAGUACGU-UUAUCAAUU-3' (SEQ ID NO:10), 5'-UAGUAGCGCUUAGUGAAUAUU-3' (SEQ ID NO:11); pool 2: 5'-AUGCACAAUUAGUUCGAGAUU-3' (SEQ ID NO:12), 5'-UAUGAUAGACGACGAGAAUUU-3' (SEQ ID NO:13), 5'-CAGACAAUGAGAACCGAAUUU-3' (SEQ ID NO:14), 5'-CGCCACAGACACCGAGAAUUU-3' (SEQ ID NO:15)). Control siRNAs included anti-cyclophilin B, and non-targeting siRNA (both Dhannacon). All transfections were carried out using Lipofectamine RNAiMax (1 µl/pmol siRNA) at a final concentration of 100 nM. siRNA complexes were formed in Optimem. Cells were lysed for analysis 72-96 hours post-transfection.

Western Blot Analysis.

Cells were washed twice with ice-cold PBS and lysed in lysis buffer (50 mM Tris-HCl pH 7.8, 1% NP-40, 10% glycerol, 150 mM NaCl, 1% Sodium deoxycholate, 1% sodium dodecyl sulfate) supplemented with protease inhibitor, phosphatase inhibitor cocktail, and EDTA (Pierce Biotechnologies). The protein content of the lysates was determined by the BCA Protein Assay Reagent (Pierce Biotechnologies). 5-20 µg of protein were separated by SDS-PAGE, transferred on to Immobilon-P membrane (Millipore) for immunodetection. Primary antibodies used were: pERK (E-4, Santa Cruz Biotechnology), cyclin D1 (M-20, Santa Cruz Biotechnology) and GNAQ (C-19, Santa Cruz biotechnology), Phospho-Akt (736E11, Cell signaling), Cyclophilin B (Abcam), anti-FLAG M2 (Sigma), Anti-ERK ½ pAb (Promega), and β-actin (Sigma). Horseradish peroxidase-labeled goat anti-mouse or anti-rabbit (Upstate) were used as secondary antibodies.

Statistical Analysis

Immunofluorescence data and CyQUANT measurements were analyzed using Student's t-test. Fisher's Exact test was used to compare the proportion of atypical cells.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Exemplary GNAQ Sequences:

SEQ ID NO: 1

Accession Number NM_002072 human guanine nucleotide binding protein (G protein) q (GNAQ), mRNA

```
   1 aggggtgcc ggcggggctg cagcggaggc actttggaag aatgactctg gagtccatca
  61 tggcgtgctg cctgagcgag gaggccaagg aagcccggcg gatcaacgac gagatcgagc
 121 ggcagctccg cagggacaag cgggacgccc gcgggagct caagctgctg ctgctcggga
 181 caggagagag tggcaagagt acgtttatca agcagatgag aatcatccat gggtcaggat
 241 actctgatga agataaaagg ggcttcacca agctggtgta tcagaacatc ttcacggcca
 301 tgcaggccat gatcagagcc atggacacac tcaagatccc atacaagtat gagcacaata
 361 aggctcatgc acaattagtt cgagaagttg atgtggagaa ggtgtctgct tttgagaatc
 421 catatgtaga tgcaataaag agtttatgga atgatcctgg aatccaggaa tgctatgata
 481 gacgacgaga atatcaatta tctgactcta ccaaatacta tcttaatgac ttggaccgcg
 541 tagctgaccc tgcctacctg cctacgcaac aagatgtgct tagagttcga gtccccacca
 601 cagggatcat cgaataccc tttgacttac aaagtgtcat tttcagaatg gtcgatgtag
 661 ggggccaaag gtcagagaga agaaaatgga tacactgctt tgaaaatgtc acctctatca
 721 tgtttctagt agcgcttagt gaatatgatc aagttctcgt ggagtcagac aatgagaacc
 781 gaatggagga aagcaaggct ctctttagaa caattatcac ataccctgg ttccagaact
 841 cctcggttat tctgttctta aacaagaaag atcttctaga ggagaaaatc atgtattccc
 901 atctagtcga ctacttccca gaatatgatg accccagag agatgcccag gcagcccgag
 961 aattcattct gaagatgttc gtggacctga acccagacag tgacaaaatt atctactccc
1021 acttcacgtg cgccacagac accgagaata tccgctttgt ctttgctgcc gtcaaggaca
1081 ccatcctcca gttgaacctg aaggagtaca atctggtcta attgtgcctc ctagacaccc
1141 gccctgccct tccctggtgg gctattgaag atacacaaga gggactgtat ttctgtggaa
1201 aacaatttgc ataatactaa tttattgccg tcctggactc tgtgtgagcg tgtccacaga
1261 gtttgtagta aatattatga ttttatttaa actattcaga ggaaaaacag aggatgctga
1321 agtacagtcc cagcacattt cctctctatc ttttttttag gcaaaacctt gtgactcagt
1381 gtattttaaa ttctcagtca tgcactcaca aagataagac ttgtttcttt ctgtctctct
1441 ctcttttttct tttctatgga gcaaaacaaa gctgatttcc cttttttctt ccccgctaa
1501 ttcataccct ccctcctgatg ttttttccccag gttacaatgg cctttatcct agttccattc
1561 ttggtcaagt tttctctca aatgatacag tcaggacaca tcgttcgatt taagccatca
1621 tcagcttaat ttaagtttgt agttttgct gaaggattat atgtattaat acttacggtt
1681 ttaaatgtgt tgctttggat acacacatag tttctttttt aatagaatat actgtcttgt
1741 ctcactttgg actgggacag tggatgccca tctaaaagtt aagtgtcatt tcttttagat
1801 gtttaccttc agccatagct tgattgctca gagaaatatg cagaaggcag gatcaaagac
1861 acacaggagt cctttctttt gaaatgccac gtgccattgt ctttcctccc ttctttgctt
1921 cttttttctta ccctctcttt caattgcaga tgccaaaaaa gatgccaaca gacactacat
1981 taccctaatg gctgctaccc agaacctttt tataggttgt tcttaatttt tttgttgttg
2041 ttgttcaagc ttttccttc ttttttttct tagtgtttgg gccacgattt taaaatgact
2101 tttattatgg gtatgtgttg ccaaagctgg cttttttgtca aataaaatga atacgaactt
2161 aaaaaataaa aaaaaaaaaa aaaaaaa
```

-continued

SEQ ID NO: 2
Accession Number NP_002063.2 guanine nucleotide binding
protein (G protein), q polypeptide [Homo sapiens]

```
  1 mtlesimacc lseeakearr indeierqlr rdkrdarrel klllllgtges gkstfikqmr 61 iihgsgysde dkrgftklvy qniftamqam iramdtlkip ykyehnkaha qlvrevdvek 121 vsafenpyvd aikslwndpg iqecydrrre yqlsdstkyy lndldrvadp aylptqqdvl 181 rvrvpttgii eypfdlqsvi frmvdvggqr serrkwihcf envtsimflv alseydqvlv 241 esdnenrmee skalfrtiit ypwfqnssvi lflnkkdlle ekimyshlvd yfpeydgpqr 301 daqaarefil kmfvdlnpds dkiiyshftc atdtenirfv faavkdtilq lnlkeynlv
```

---

What is claimed is:

1. A method of identifying a human patient having a melanocytic neoplasm that is a candidate for receiving a GNAQ antagonist, wherein the melanocytic neoplasm is a blue nevus, a uveal melanoma, or a melanoma that arose from a blue nevus or from chronic sun damaged skin, the method comprising:
   providing a nucleic acid sample from the melanocytic neoplasm;
   detecting whether a mutation at a codon encoding Gln 209 in a GNAQ gene encoding SEQ ID NO:2 is present in the nucleic acid sample;
   identifying the patient as a candidate for receiving a GNAQ antagonist when the mutation at the codon encoding Gln 209 is present.

2. The method of claim 1, wherein the mutation is a Q209L or Q209P substitution.

3. The method of claim 1, wherein the detecting step comprises contacting the nucleic acid sample with a probe that selectively hybridizes to the GNAQ gene, and detecting the presence of hybridized probe, thereby detecting the sequence mutation.

4. The method of claim 3, wherein the contacting step is performed in an in situ hybridization.

5. The method of claim 1, wherein the detecting step comprises an amplification reaction.

6. The method of claim 1, wherein the detecting step comprises sequencing the mutated region of the GNAQ gene.

7. The method of claim 1, wherein the biological sample is an eye sample, or a skin sample.

8. The method of claim 1, wherein the biological sample is from lymph node, lung, liver, adrenal gland, soft tissue, or bone.

9. The method of claim 1, wherein biological sample is from a patient that has melanoma.

10. The method of claim 9, wherein the melanoma is a uveal melanoma.

11. A method of identifying a human patient having a blue nevus that is at risk of progressing to a melanoma, the method comprising detecting the presence or absence of a sequence mutation in a codon encoding Gln 209 in a GNAQ gene encoding SEQ ID NO:2 in a nucleic acid sample from the nevus, and identifying the patient as having a blue nevus that is at risk of progressing to melanoma when the mutation is present.

12. The method of claim 11, wherein the mutation is a Q209L or Q209P substitution.

13. The method of claim 11, wherein the detecting step comprises contacting the nucleic acid sample with a probe that selectively hybridizes to the GNAQ gene, and detecting the presence of hybridized probe, thereby detecting the sequence mutation.

14. The method of claim 13, wherein the contacting step is performed in an in situ hybridization.

15. The method of claim 11, wherein the detecting step comprises an amplification reaction.

16. The method of claim 11, wherein the detecting step comprises sequencing the mutated region of the GNAQ gene.

17. A method of identifying a human patient having a melanocytic neoplasm that is a candidate for receiving a GNAQ antagonist, wherein the melanocytic neoplasm is a blue nevus, a uveal melanoma, or a melanoma that arose from a blue nevus or from chronic sun damaged skin, the method comprising:

providing a nucleic acid sample from the melanocytic neoplasm;

detecting whether a Q209L sequence mutation is present at a codon encoding Gln 209 in a GNAQ gene encoding SEQ ID NO:2 in the nucleic acid sample;

identifying the patient as a candidate for receiving a GNAQ antagonist when the mutation at the codon encoding Gln 209 is present.

18. The method of claim 17, wherein the detecting step comprises contacting the nucleic acid sample with a probe that selectively hybridizes to the GNAQ gene, and detecting the presence of hybridized probe, thereby detecting the sequence mutation.

19. The method of claim 18 wherein the contacting step is performed in an in situ hybridization.

20. The method of claim 17, wherein the detecting step comprises an amplification reaction.

21. The method of claim 17, wherein the detecting step comprises sequencing the mutated region of the GNAQ gene.

22. The method of claim 17, wherein the biological sample is an eye sample, or a skin sample.

23. The method of claim 17, wherein the biological sample is from lymph node, lung, liver, adrenal gland, soft tissue, or bone.

24. The method of claim 17, wherein biological sample is from a patient that has melanoma.

25. The method of claim 24, wherein the melanoma is a uveal melanoma.

* * * * *